United States Patent
Shohat

(10) Patent No.: US 10,201,325 B2
(45) Date of Patent: Feb. 12, 2019

(54) CONTROLLED TISSUE DISSECTION SYSTEMS AND METHODS

(75) Inventor: Shaul Shohat, Kfar HaOranim (IL)

(73) Assignee: BIOPROTECT LTD., Kokhav Ya'ir (IL)

( * ) Notice: Subject to any disclaimer, the term of this patent is extended or adjusted under 35 U.S.C. 154(b) by 728 days.

(21) Appl. No.: 13/521,080

(22) PCT Filed: Jan. 6, 2011

(86) PCT No.: PCT/IL2011/000018
§ 371 (c)(1),
(2), (4) Date: Jul. 9, 2012

(87) PCT Pub. No.: WO2011/083474
PCT Pub. Date: Jul. 14, 2011

(65) Prior Publication Data
US 2012/0330340 A1    Dec. 27, 2012

Related U.S. Application Data

(60) Provisional application No. 61/292,899, filed on Jan. 7, 2010, provisional application No. 61/412,490, filed on Nov. 11, 2010.

(51) Int. Cl.
*A61M 29/02* (2006.01)
*A61B 8/12* (2006.01)
(Continued)

(52) U.S. Cl.
CPC ............... *A61B 8/12* (2013.01); *A61B 8/445* (2013.01); *A61B 17/320016* (2013.01); *A61B 2017/320048* (2013.01); *A61B 2034/107* (2016.02)

(58) Field of Classification Search
CPC .... A61L 8/12; A61L 8/445; A61L 17/320016; A61L 2019/507; A61L 2017/320048
See application file for complete search history.

(56) References Cited

U.S. PATENT DOCUMENTS 5,720,762 A * 2/1998 Bass .............................. 606/192
6,015,382 A * 1/2000 Zwart et al. .................. 600/207
(Continued)

FOREIGN PATENT DOCUMENTS

WO    9912602 A1    3/1999
WO    0072760 A1    12/2000
(Continued)

OTHER PUBLICATIONS

International Preliminary Report on Patentability dated Jul. 19, 2012 From the International Bureau of WIPO Re. Application No. PCT/IL2011/000018.
(Continued)

*Primary Examiner* — Anh Dang
(74) *Attorney, Agent, or Firm* — Marc Van Dyke; Fourth Dimension IP

(57) ABSTRACT

Tissue dissecting device, including an inflatable bladder configured to be inserted into a body via an introducer tube in a compact deflated state, and to be inflated to a substantially planar form in a manner which dissects tissue. Method for dissecting tissue, including inserting an inflatable bladder, in a deflated state, via an introducer tube, into a space in a body, and inflating the bladder to substantially planer form, thereby dissecting tissue. Method for dissecting tissue, including inserting an introducer tube via an incision into a body, inserting an inflatable bladder, in a defined state, via the introducer tube, into a space in the body, pulling the introducer tube back at least a length of the deflated bladder, inflating the bladder, via a filling tube, to substantially planar form, thereby dissecting tissue, disconnecting the filling tube from the bladder, retracting the filling tube and the introducer tube from the body.

10 Claims, 19 Drawing Sheets

(51) Int. Cl.
*A61B 8/00* (2006.01)
*A61B 17/32* (2006.01)
*A61B 34/10* (2016.01)

(56) References Cited

U.S. PATENT DOCUMENTS

| | | | |
|---|---|---|---|
| 6,361,543 B1 * | 3/2002 | Chin | A61B 17/0218 600/207 |
| 7,041,050 B1 * | 5/2006 | Ronald | 600/104 |
| 2004/0049223 A1 | 3/2004 | Nishtala et al. | |
| 2004/0254625 A1 * | 12/2004 | Stephens et al. | 623/1.1 |
| 2006/0064059 A1 | 3/2006 | Gelfand et al. | |
| 2007/0060814 A1 | 3/2007 | Stafford | |
| 2008/0033471 A1 * | 2/2008 | Paz et al. | 606/190 |
| 2008/0097506 A1 | 4/2008 | Criscuolo et al. | |
| 2009/0048537 A1 | 2/2009 | Lydon et al. | |
| 2009/0088789 A1 | 4/2009 | O'Neil et al. | |
| 2009/0171157 A1 | 7/2009 | Diederich et al. | |
| 2009/0182368 A1 | 7/2009 | Lunsford et al. | |

FOREIGN PATENT DOCUMENTS

| | | |
|---|---|---|
| WO | 2007075375 | 7/2007 |
| WO | WO 2011/083474 | 7/2011 |

OTHER PUBLICATIONS

International Search Report and the Written Opinion dated Aug. 2, 2011 From the International Searching Authority Re. Application No. PCT/IL2011/000018.
Amended claims filed after receipt of PCT search report for EP2521586—claims filed Aug. 7, 2012.
Supplementary European Search Report for EP2521586 dated May 17, 2013.
European Search Opinion for EP2521586 dated May 17, 2013.

* cited by examiner

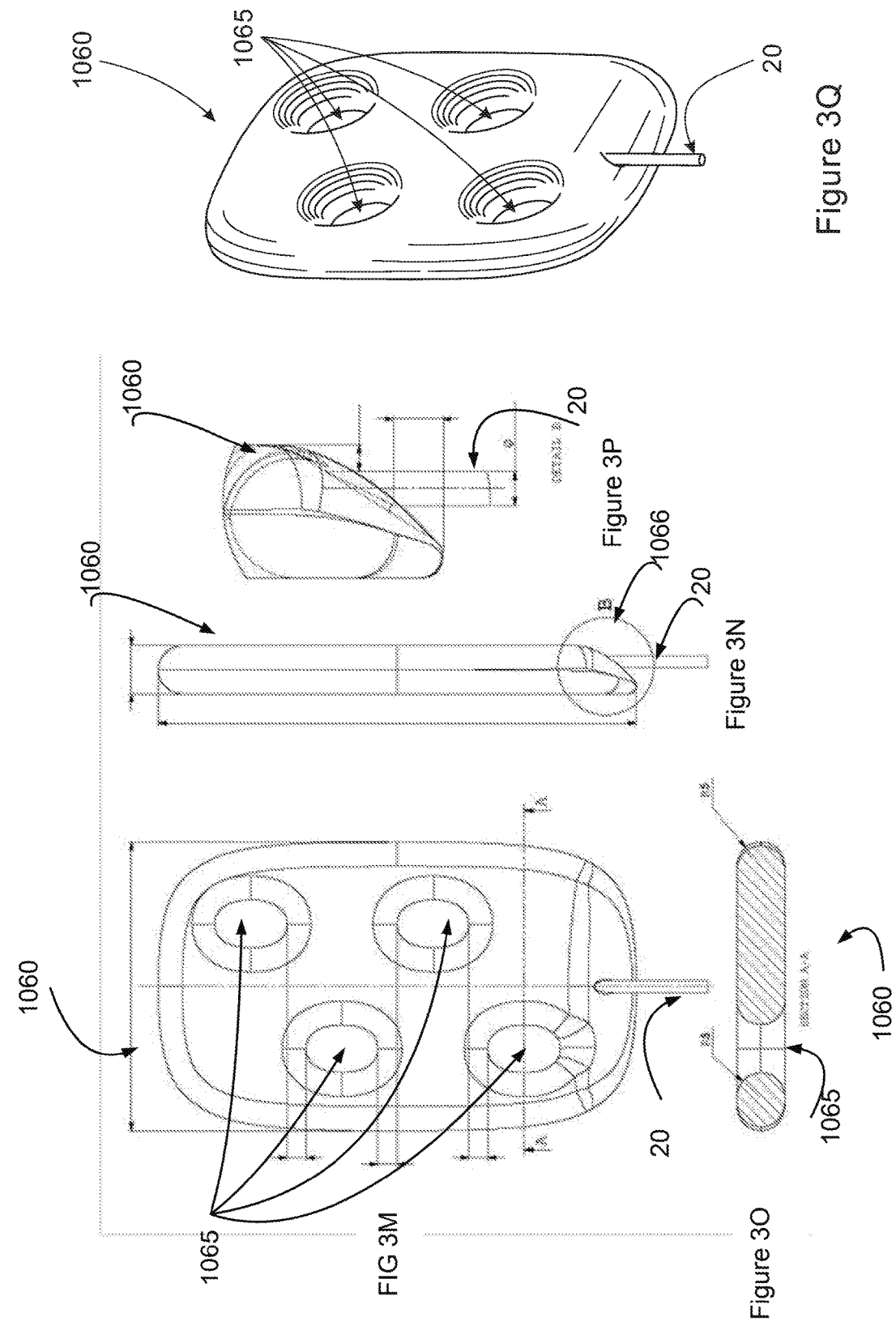

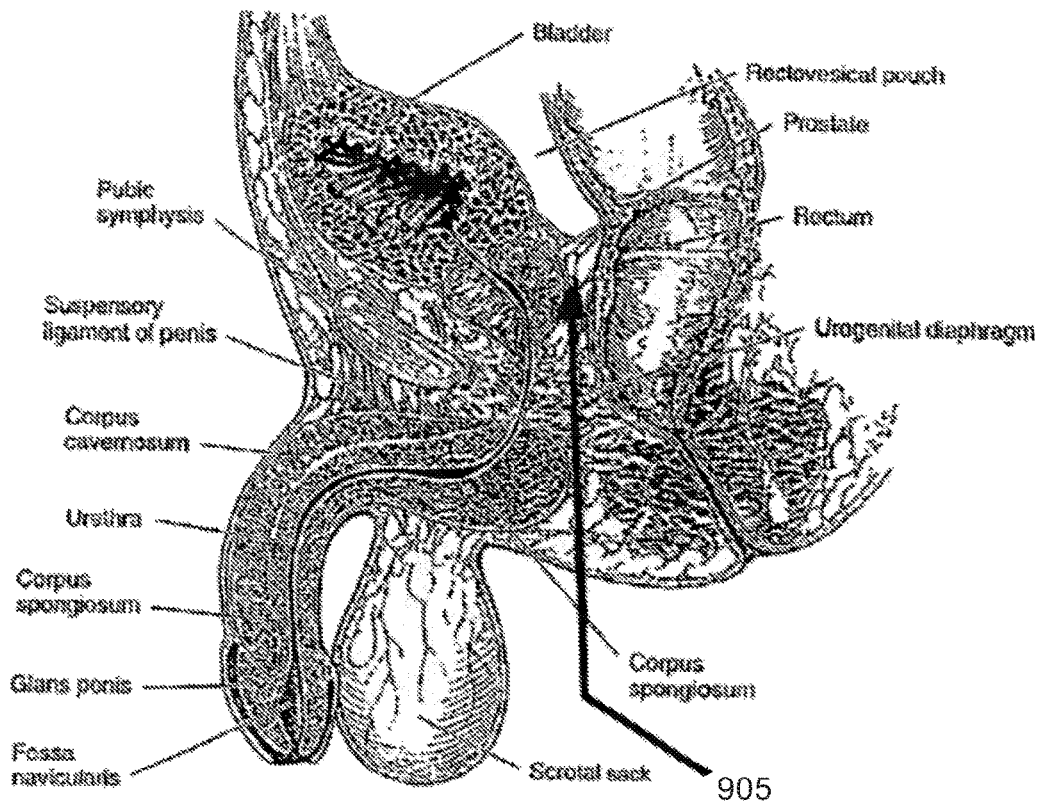
Figure 9A
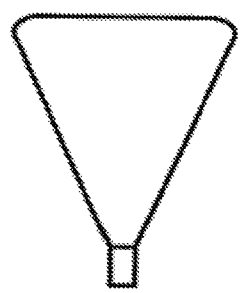 
Figure 9B    Figure 9C

CONTROLLED TISSUE DISSECTION SYSTEMS AND METHODS

RELATED APPLICATIONS

This application is a National Phase of PCT Patent Application No. PCT/IL2011/000018 having International filing date of Jan. 6, 2011, which claims the benefit of priority under 35 USC § 119(e) of U.S. Provisional Patent Application No. 61/292,899 filed on Jan. 7, 2010, and of U.S. Provisional Patent Application No. 61/412,490 filed on Nov. 11, 2010. The contents of the above applications are all incorporated herein by reference as if fully set forth herein in their entirety.

FIELD AND BACKGROUND OF THE INVENTION

The present invention, in some embodiments thereof, relates to expandable tissue dissecting devices, and, more particularly but not exclusively, to directionally controllable inflatable, optionally implantable, bladders configured for tissue dissection.

Dissecting and/or separating tissue layers are common techniques for placing implants and/or surgical devices inside a patient's body, as well as for removing unwanted tissues and organs. One such technique is commonly performed during surgical intervention for organ support, such as, for example, for mid-urethral support and/or prolapse prevention, where a mesh or other implant type is introduced for treating and/or preventing prolapse.

Dissection is also used for safely deploying medical devices and/or implants for protecting and/or treating tissue, for example during radiation therapy. Removal or treatment of pathological tissue such as cancer or malignant or benign growth or tumor caused by abnormal or uncontrolled cell division can be effected in any one of several well known approaches. A common form of treatment is surgery, followed by radiation (external or internal), chemical and thermal therapies. Examples of radiation therapies include but are not limited to external radiation beam therapy and interstitial brachytherapy, a technique in which radioactive sources are placed into a body, for example into the prostate gland, delivering radiation from within the prostate.

Prostate cancer is a common malignancy in men worldwide, with about 220,000 new cases diagnosed each year in the US alone. Each year, about 50,000 US patients undergo radical prostatectomy, in which all or part of the prostate gland is surgically removed. Over the last few years there is an increasing trend to use minimally invasive techniques such as laparoscopic radical prostatectomy (LRP).

Radical prostatectomy represents a delicate operation with a long learning curve, especially when are performed laparoscopically or by robotic surgery, where the learning curve may consist of 50 to 200 cases. One of the most challenging phases of the operation is a dissection and/or separation of the prostate from the rectal wall, where in laparoscopy or robotic surgery the practitioner's tactile sense is not effective.

Erectile nerves pass laterally to the prostate in close proximity to the superior and lateral vascular pedicles of the prostate. In order to preserve these nerves, the vascular supply to the prostate has to be sectioned close to the lateral margins of the prostate.

The prostate and surrounding tissues, as well as the space between rectum and prostate, may be visualized under high resolution using such modalities such as Trans-Rectal Ultra-Sound (TRUS), MRI or CT. Additionally, urologists, interventional radiologists, and oncologists performing brachytherapy, are well accustomed to performing prostate biopsies and insertion of brachytherapy seeds through the perineum under TRUS guidance.

Separation of the prostate from the rectum is also performed during treatment of the prostate by other modalities such as ionizing radiation (external beam radiation or brachytherapy), thermal ablation, cryoablation, chemical ablation, electroporation, biological therapy with immunologic cell or vaccines, etc. These approaches can be practiced individually or in combination as adjuvant therapy.

In any case, the treatment procedure carries some degree of risk of injury to healthy tissues. For example, during surgery, use of surgical instruments in small, tight spaces can lead to inadvertent tissue injury. Radiation therapy or localized release of chemical substances can result in an intensity gradient between treated tissue and healthy tissue, and radiation or chemical injury to healthy tissues. As a result, a total energy or chemical dose for local treatment which should be applied to a tissue is limited by a dose which may be transmitted to healthy adjacent tissues. Moreover, some tissues and organs are more sensitive to radiation and chemical damage than others, and thus treatment of tissue adjacent to such tissues and organs can be severely limited.

Additional background art includes:

U.S. Pat. No. 6,852,095 to Ray;
Published U.S. Patent Application No. 2008/0033471 of Paz et al;
Published U.S. Patent Application No. 2008/111078 of Shohat;
PCT Published Patent Application WO/06001009 of Paz et al;
PCT Published Patent application WO/2008/111078 of Shohat; and
"The Seldinger technique", a reprint from Acta Radiologica 1953; AJR Am J Roentgenol. 1984 January; 142(1):5-7.

SUMMARY OF THE INVENTION

The present invention, in some embodiments thereof, relates to a tissue dissecting device which includes an inflatable bladder for dissecting tissue, and, more particularly but not exclusively, to an inflatable bladder which also serves for separating tissue, and/or optionally remains in a body as an implant.

In an exemplary embodiment of the invention, the tissue dissecting device includes an inflatable bladder configured to be inserted into a body in a collapsed, deflated state, to be inflated to dissect tissue while unrolling/unfurling and otherwise extending the bladder.

Some embodiments of the invention include a method for dissecting tissue, including inserting an inflatable bladder, in a deflated state, into a space in a body, inflating the bladder to a substantially planar form, and further inflating the bladder, thereby dissecting tissue with an edge of the bladder.

According to an aspect of some embodiments of the invention, there is provided a tissue dissecting device, including an inflatable bladder deployable in a deflated and wrapped formation in a post-hydrodissected space between a prostate and a rectal wall, wherein the bladder having a first unwrapping stage when inflated to a first volume thereby regaining a substantially flattened formation while dissecting a tissue and/or in-between tissue layers. In some embodiments such expansion is limited to a specific 2D or 3D expansion pattern and/or final shape and/or size.

According to an aspect of some embodiments of the present invention there is provided a tissue dissecting device, including an inflatable bladder configured to be inserted into a body via an introducer tube in a compact deflated state, and to be inflated to a substantially planar form in a manner which dissects tissue.

According to some embodiments of the invention, the bladder is configured to be inflated in a manner which dissects in between tissues.

According to some embodiments of the invention, the inflatable bladder is provided rolled in the compact deflated state.

According to some embodiments of the invention, the inflatable bladder is provided as double inwardly rolled wings in the compact deflated state.

According to some embodiments of the invention, the bladder is configured to unroll when inflated, thereby to dissect the tissue by elongation of the compact state of the bladder.

According to some embodiments of the invention, thickness of the bladder in the substantially planar form is substantially a diameter of the bladder when in the compacted deflated state.

According to some embodiments of the invention, further including an introducer tube configured for guiding the bladder in the deflated state to a target location in a body.

According to some embodiments of the invention, the compact deflated state of the bladder fits inside an introducer tube having an inner diameter of less than 10 millimeters.

According to some embodiments of the invention, the compact deflated state of the bladder fits inside an introducer tube having an inner diameter of 2-3 millimeters.

According to some embodiments of the invention, further including a restrictor connected to the bladder and configured to restrict motion of the bladder along a connection of the bladder to the restrictor.

According to some embodiments of the invention, the restrictor is connected to the bladder by a biodegradable connector.

According to some embodiments of the invention, the connector includes a hinge configured to allow relative motion between the restrictor and the bladder around a chosen axis.

According to some embodiments of the invention, the bladder includes at least one substantially slippery surface with respect to the tissue.

According to some embodiments of the invention, the inflatable bladder is coated by a substantially slippery coating.

According to some embodiments of the invention, material constructing the inflatable bladder includes a mix of Poly Lactic Acid (PLA) and Poly Capro Lactone.

According to some embodiments of the invention, the bladder is configured to laterally expand by inflation, dissecting the tissue.

According to some embodiments of the invention, the substantially planar form is shaped to substantially fit into a specifically shaped space in a body.

According to some embodiments of the invention, further including a mesh attached to a surface of the inflatable bladder.

According to some embodiments of the invention, the substantially planar form is shaped to substantially fit into a space between a prostate and a rectal wall.

According to some embodiments of the invention, the bladder in the compact deflated state is shaped to substantially fit into a post-hydrodissection space between a prostate and a rectal wall.

According to some embodiments of the invention, further including two opposing faces of the inflatable bladder being connected to each other by a portion of their inner surfaces, and limiting maximum thickness of the bladder.

According to some embodiments of the invention, further including two opposing faces of the inflatable bladder being connected to each other by at least one through hole in each of the two opposing faces, in which edges of the hole are formed of the two opposing faces being attached to each other, and limiting maximum thickness of the bladder.

According to an aspect of some embodiments of the present invention there is provided a method for dissecting tissue, including inserting an inflatable bladder, in a deflated state, via an introducer tube, into a space in a body, and inflating the bladder to a substantially planar form, thereby dissecting tissue.

According to some embodiments of the invention, dissecting tissue includes dissecting connecting tissue between organs.

According to some embodiments of the invention, the deflated state includes a rolled-up bladder.

According to some embodiments of the invention, the deflated state includes a bladder rolled up as double inward rolled wings.

According to some embodiments of the invention, the bladder is configured to unroll when inflated, thereby to dissect the tissue by elongation of the compact state of the bladder.

According to some embodiments of the invention, thickness of the bladder is substantially constant throughout the inflating.

According to some embodiments of the invention, further including using a restrictor connected to the bladder to restrict motion of the bladder along a connection of the bladder to the restrictor.

According to some embodiments of the invention, the restrictor is connected to the bladder by a connector configured to allow relative motion between the restrictor and the bladder around a chosen axis.

According to some embodiments of the invention, the inflating causes the bladder to expand laterally, thereby dissecting the tissue with an edge of the bladder.

According to some embodiments of the invention, the substantially planar form is shaped to substantially fit into a specifically shaped space in a body.

According to some embodiments of the invention, the inflation is performed by injecting liquid into the bladder.

According to some embodiments of the invention, further including leaving the bladder in the body.

According to some embodiments of the invention, the bladder includes a mesh.

According to some embodiments of the invention, further including creating an opening in-between tissue layers.

According to some embodiments of the invention, further including creating a hydrodissected tissue space between a prostate and a rectal wall.

According to some embodiments of the invention, further including using a motorized mechanism to displace the introducer tube.

According to some embodiments of the invention, further including using a processor to control the motorized displacement.

According to some embodiments of the invention, the processor is used to control the inflation of the bladder.

According to some embodiments of the invention, the processor is used to interface to a Trans-Rectal Ultrasound (TRUS) probe.

According to an aspect of some embodiments of the present invention there is provided a method for dissecting tissue, including inserting an introducer tube via an incision into a body, inserting an inflatable bladder, in a deflated state, via the introducer tube, into a space in the body, pulling the introducer tube back at least a length of the deflated bladder, inflating the bladder, via a filling tube, to a substantially planar form, thereby dissecting tissue, disconnecting the filling tube from the bladder, retracting the filling tube and the introducer tube from the body.

According to an aspect of some embodiments of the present invention there is provided a tissue dissecting device configured for creating a planar physical barrier in-between previously connected tissue layers, the device including:

(1) upper and lower outer surfaces at least partially connected along a circumference, and (2) means for outwardly displacing a portion of the surfaces to a predefined distance, wherein the surfaces are provided in-contact and in an inwardly rolled formation having a thickness, wherein the surfaces are adapted to unroll when the outwardly displaced portion thereof is forced to laterally increase until a full planar formation is met and the surfaces are parallel and distant by the predefined distance, and wherein the predefined distance is substantially the same as the thickness.

According to some embodiments of the invention, further including an inlet port located in-between the upper and lower surfaces, wherein the means include a fluid pressurizing device and a channel detachably connectable between the fluid pressurizing device and the inlet port and configured to accommodate fluid flow therethrough between the upper and lower surfaces.

According to some embodiments of the invention, the inwardly rolled formation is a double asymmetric rolled formation.

According to some embodiments of the invention, including an inflatable chamber.

According to some embodiments of the invention, including a biodegradable portion.

According to some embodiments of the invention, sized and configured to dissect and provide a physical barrier between adjacent tissues of prostate and rectum.

According to some embodiments of the invention, further including a mesh connected to one of the outer surfaces.

According to some embodiments of the invention, further including means to align the surfaces to the channel, thereby limiting surfaces unrolling to a defined plane.

According to some embodiments of the invention, the predefined distance is equal or less than 15 mm.

According to some embodiments of the invention, further including connective means to connect central portions of the surfaces thereby limiting a maximal distance between the central portions to the predefined distance.

According to some embodiments of the invention, the connective means include at least one through hole in each of the surfaces, in which edges of the hole are formed of the surfaces being attached to each other.

According to an aspect of some embodiments of the invention, there is provided a tissue dissecting device, including an inflatable bladder deployable in a deflated and wrapped formation in a post-hydrodissected space between a prostate and a rectal wall, wherein the bladder having a first unwrapping stage when inflated to a first volume thereby regaining a substantially flattened formation, a second expansion stage indicative in a 3D expansion when inflated up to a second volume, and a third spreading stage indicative in a 2D expansion when inflated over the second volume, whereby the 2D expansion accompanies a lateral dissection of adjacent tissues in the space.

In some embodiments, the tissue dissecting device includes means to limit expansion of the bladder in one axis when inflated over the second volume. In some embodiments, the bladder is implantable.

According to an aspect of some embodiments of the invention, there is provided a tissue dissecting device including:

(a) an expandable implantable bladder having a predetermined initial state and a final state differentiated by width, height and formation;

(b) a catheter releasably attached to the bladder further adaptable for guiding the bladder to a target location in body; and (c) a restrictor coupled to the catheter and adapted to restrict motion of the bladder in at least one axis during and/or after transformation thereof from the initial state to the final state, wherein the catheter and restrictor are adapted to be disassociated from the bladder after the transformation thereof.

In some embodiments, the bladder is biodegradable.

In some embodiments, the bladder in its initial formation is substantially tubular and provided flattened and rolled.

In some embodiments, the bladder in its initial formation is provided as double inwardly rolled wings.

In some embodiments, the bladder in its initial formation is equal or less than 3 mm in diameter.

In some embodiments, the catheter including a lumen adapted to directly communicate between external inflation means with an internal chamber of the balloon.

In some embodiments, the restrictor is adapted to restrict lateral motions of the implant.

In some embodiments, the restrictor is adapted to restrict rotational motions of the implant with respect to the catheter.

In some embodiments, the restrictor is adapted to restrict vertical motions of the implant with respect to the catheter.

In some embodiments, the restrictor including a substantially rigid strip distally extended from the catheter over a first surface of the implant.

In some embodiments, the restrictor is adapted to restrict expansion of the implant in the direction of the first surface.

In some embodiments, the dissecting device further includes a motorized mechanism adapted to displace the catheter and/or a processor adapted to order and control the displacement, and/or a TRUS probe.

In some embodiments, the bladder includes integral expansion restricting means.

In some embodiments, the integral expansion restricting means includes at least one inelastic pliable strip internally connecting between a first and a second surface of the implant, thereby restricting the expansion to the predetermined final width and/or height.

In some embodiments, the integral expansion restricting means includes at least one through hole periphery line firmly attaching two parallel surfaces of the implant along a length thereof, thereby restricting the expansion to the predetermined final width and/or height.

In some embodiments, the bladder is seamless.

In some embodiments, the bladder is non-compliant.

In some embodiments, the bladder includes an elastic wall portion.

In some embodiments, the catheter is connected to the bladder through a rigid biodegradable connector.

In some embodiments, connector includes a hinge adapted to allow relative motion between said catheter and said implant only at chosen axes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3M-3P are simplified illustrations of alternative embodiments of an inflatable bladder, constructed and operating according to an example embodiment of the present invention;

FIG. 3Q is a simplified illustration of a 3D model of the inflatable bladder of FIGS. 3M-3P;

FIG. 9A is a simplified illustration of an example location for using a tissue dissecting device according to an example embodiment of the present invention;

FIGS. 9B and 9C are simplified illustrations of a top view and a side view of an inflatable bladder constructed according to an example embodiment of the present invention;

FIG. 12 is a simplified illustration of an inflatable bladder including an external restrictor according to an example embodiment of the present invention.

DESCRIPTION OF SPECIFIC EMBODIMENTS OF THE INVENTION

Figure 1A:
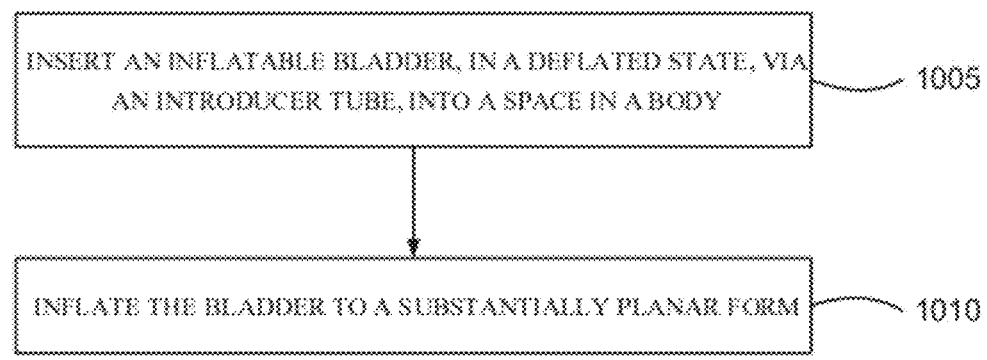
FIG. 1A is a simplified flow chart illustration of a method of tissue dissection according to an example embodiment of the present invention.

The present invention, in some embodiments thereof, relates to expandable tissue dissecting devices, and, more particularly but not exclusively, to directionally controllable inflatable, optionally implantable, bladders configured for tissue dissection.

The present invention, in some embodiments thereof, relates to controllably expandable/spreadable tissue dissecting devices, and, more particularly but not exclusively, to an inflatable bladder which also serves for dissecting tissue, and optionally also remains in a body as an implant.

Tissue dissection, and specifically planar dissection in-between tissue layers, is a procedure used in various surgical applications. Some of the exemplary embodiments presented herein generally correspond to dissection in the vicinity of the prostate gland, for illustrative and not binding purposes. It is noted that the description of the present invention is not intended to be limited to the vicinity of the prostate gland, and that other body locations are contemplated as using embodiments of the present invention. Nevertheless, examples are made with reference to the vicinity of the prostate gland, in order to provide a more detailed description.

In some such cases, especially but not exclusively when treatment comprises more than one session, possibly performed during a few days or weeks, such an inflatable bladder may be implanted in an at least partially expanded state. The bladder may be left in-place during at least the period of the treatment sessions and even permanently. The bladder may be configured to degrade and/or be absorbed after treatments end.

In modern practice it is commonly preferred to introduce surgical instrumentation using minimally invasive techniques and to perform the procedure with minimal harm to non-target tissues. In some embodiments of the present invention the dissecting device is introduced in a minimally invasive approach (e.g., a "key hole" introduction) when collapsed to a miniature size, and then deployed by expanding/spreading the device in a highly controllable fashion in specific sizes and directions, thereby avoiding harm to adjacent organs and tissues, while performing the dissection. In some instances, it may be desirable to prepare the target location prior to dissector introduction, for example by creating an initial space and/or by expanding tissue, such as by using hydrodissection.

Insertion of an inflatable bladder using conventional brachytherapy templates is sometimes problematic since such templates permit insertion through the perineum, parallel to a TRUS probe, or at a limited combination of angle and height from the TRUS probe.

The space between the prostate and rectum may be very narrow, sometimes 1-2 mm at most; may be at an angle with respect to the rectal wall; may have one or more curvatures in a longitudinal direction, especially in large prostates; and may further be curved in the axial or transverse plane.

Some embodiments of the invention provide a versatile guiding system which enables accurate positioning of such a separator or spacer between the rectum and prostate.

Some embodiments of the invention include an introducer for such an inflatable bladder, which may optionally be provided with ways for preventing displacement of the inflatable bladder during expansion or inflation.

In an example embodiment of the invention the inflatable bladder is used as a tissue separator to dissect and/or separate the prostate from the rectum and permit sectioning and closure of the superior and lateral pedicles of the prostate while sparing the erectile nerves.

In an example embodiment of the invention the inflatable bladder is introduced using a minimally invasive method through the perineum under TRUS guidance.

In an example embodiment of the invention the inflatable bladder attains the size and shape of the interface between the prostate and rectum while applying minimal forces on the anterior rectal wall during such expansion.

In an example embodiment of the invention the inflatable bladder optionally includes a mechanical and electronic guiding system for introducing such device accurately.

In an example embodiment of the invention the inflatable bladder provides a method for accurately implanting and deploying a tissue dissecting device.

The inflatable bladder optionally operates as a tissue dissecting device for dissecting in-between two tissue parts by uniform, centered and controlled lateral expansion, while maintaining a limit on a maximal allowed height. In some cases, such lateral expansion should progress under substantial resistance, sometimes mostly or even solely lateral. In some cases, only lateral dissecting forces applied by the device are allowed.

Overview of Some Embodiments

The present invention, in some embodiments thereof, includes a tissue dissecting device, comprising an inflatable bladder configured to be inserted into a body in a compact, deflated state, to be inflated to expand to a substantially planar form, and by expanding, to dissect tissue.

In some embodiments, the device is a deflated bladder which is rolled-up and dissects the tissue by unrolling as it is inflated. The unrolling can be similar to a party favor known as a noisemaker, which unrolls when inflated.

In some embodiments, the device is a memory material, such as Nitinol, which is inserted in a compact form, and caused to expand within the body.

In some embodiments, the device is a mechanically expandable cage, which is inserted in a compact form, and caused to expand within the body.

In some embodiments, the device is inserted into a slit or a small space in the body, and upon expansion, dissects in a chosen direction. In an example embodiment of the invention, the placement is selected such that the dissection works out to be dissection of a direction of less resistance, for example when dissecting connection tissue between organs, typically leaving the organs unharmed. Using such a device may require less manual dexterity than dissecting with a knife, and especially less manual dexterity than laparoscopic dissection. An optional first incision may be small; an introducer tube inserts the deflated, compact bladder to a safe location between organs, which can be verified by imaging. The bladder position is optional stabilized in place by an optional rigid connector to the bladder, and the bladder is inflated. The inflation causes a dissection in a direction and/or plane upon which the bladder expands. The final shape of the bladder is optionally predefined according to anatomic considerations.

When compared to simply inserting a bladder and inflating it, some embodiments of the present invention provide one or more significant advantages. The initial, intermediate, and final size and shape of the bladder is produced to be well defined and controlled. The length and width to which the bladder expands correspond to length and width desired for dissection. The thickness to which the bladder expands is limited, and in some embodiments preserved substantially constant, and designed to allow the bladder to have a well defined shape, similarly to an air mattress being inflated to a rectangular shape and not a sausage-like shape. The controlled thickness prevents undue pressure on neighboring organs.

In some embodiments, the device is configured to be laterally expanded by inflation, and to dissect the tissue by a leading edge of the bladder pushing between tissue layers of same or different organs.

The term "bladder" in all its grammatical forms is used throughout the present specification and claims interchangeably with the term "balloon" and its corresponding grammatical forms, and may also include any chamber expandable by inflation.

Limiting Thickness of the Inflated Bladder

In some embodiments, the bladder is configured to limit the thickness of the bladder in its expansion, for example as will be described in more detail below with reference to FIGS. 3H-3Q, 4 and 5. Maximal expansion thickness is optionally determined according to the anatomic target and/or the medical application. The thickness, in some embodiments, can be limited to 5 mm, 10 mm, 20 mm, 30 mm, or other higher, lower, or in-between values.

Limiting the thickness may be made by having one or more substantially non-stretchable connectors connecting two opposing sides of the inflatable bladder and limiting maximum thickness of the bladder.

In some embodiments, the bladder is configured to limit the thickness of the bladder by having two opposing faces of the inflatable bladder connected to each other by a portion of their inner surfaces, and limiting maximum thickness of the bladder.

In some embodiments, the bladder is configured to limit the thickness of the bladder by having two opposing faces of the inflatable bladder being connected to each other by at least one through hole in each of the two opposing faces, in which edges of the hole are formed of the two opposing faces being attached to each other, and limiting maximum thickness of the bladder.

In some embodiments, the number and size of thickness limiting elements is chosen according to bladder size and shape, medical application and bladder rolling scheme. In some instances it is preferable to provide a single, relatively large, through-hole type limiter, whereas in other instances it is preferred to provide a plurality of holes.

For example, for a dissecting bladder used in prostate radiation treatments, having a maximal thickness of 15 mm, there may be provided a single opening of 5 mm or less in diameter, providing acceptable radiation screening efficiency. In an exemplary dissecting bladder used in prolapse treatments, having maximal thickness between 5-20 mm, optionally 9 mm, a plurality of holes may be provided, each having a diameter of 5 mm or less. In some embodiments, hole diameter will be chosen as 1/10, optionally 1/5, optionally 1/2, optionally substantially the same, or optionally up to twice the size of a maximally expanded bladder thickness.

In some embodiments of the invention, the bladder is constructed of parallel tubes, interconnected so as to allow inflation material to pass between the tubes.

In some embodiments of the invention, the parallel tubes are laid out in a layer one tube in thickness. A shape of final inflation of the bladder is optionally substantially planar, having some thickness. The thickness of the bladder is substantially determined by a thickness of one tube, and an area and shape of the area of the bladder is substantially determined by the layout of the layer of tubes.

Material Making Up the Bladder

In some embodiments, the bladder includes materials which are flexible enough for rolling, unrolling and/or inflating.

In some embodiments, such abilities are changeable with temperature, and more specifically are present in body temperature. In some embodiments of the invention, the bladder is substantially inflexible in temperatures of up to 10, optionally 20, optionally 30 degrees Celsius, while becoming substantially flexible in temperatures over 25, optionally 35 degrees Celsius. In some embodiments of the invention, the bladder is provided deflated and collapsed (e.g., rolled) in a rigid state, and then expands without plastically deforming and/or failing in body temperature.

In some embodiments, the bladder includes biodegradable and/or bioabsorbable substances, as will be further described hereinafter.

In some embodiments of the invention, material making up the bladder is designed to be especially slippery (i.e., having small coefficient of friction), thereby providing smooth surfaces to avoid friction on tissue while unrolling or expanding.

In some embodiments of the invention, the bladder is coated with a slippery material, so as not to drag on tissue while unrolling or expanding.

In some embodiments of the invention, a slippery material is injected into the body near the bladder.

In some embodiments of the invention, the bladder is manufactured as a seamless bladder having a substantially homogenous wall thickness, by employing deep molding and/or investment casting (commonly referred to as "lost wax") techniques, such as those disclosed in above-mentioned Published U.S. Patent Application No. 2008/0033471.

Limiting Expansion

In some embodiments, the bladder is configured to limit the lateral expansion. Limiting the lateral expansion may be made by having non-expandable strips connected to opposite edges of the planar bladder, limiting how far the bladder can expand. In some embodiments, the lateral expansion is limited by limiting how much the bladder is inflated: by limiting how much fluid is pumped into the bladder; by limiting how much gas is pumped into the bladder; and/or by limiting pressure of inflation of the bladder. Finding out at what stage to limit expansion may optionally be made by imaging the bladder as it expands.

Optional Dissection by Edges of the Bladder

In some embodiments, edges of the planar bladder are configured for dissecting tissue, for example as will be described in more detail with reference to FIGS. 1G-1H.

In some embodiments, a first portion of the edge, that is some of the edge, or of the circumference of the bladder, is made tapered. In some embodiments, the first portion is configured for dissecting by having a tapered seamed edge.

Blunt Edges of the Bladder

In some embodiments, a second portion of the edge is made blunt, for example as will be described in more detail with reference to FIGS. 1I-1J. in an example embodiment of the invention the blunt portion is designed so as not to dissect where dissection is not wanted. The blunt portion optionally provides support opposite the dissecting edge, such that the lateral expansion finds support on the blunt side and provides a base against which to push while dissecting with the dissecting edge. In some embodiments, the second portion is a round edge. In some embodiments, the second portion is a rounded seamed edge.

It is noted that in some embodiments of the invention, a suitable bladder, in terms of shape, and/or thickness, and/or dissecting edges, and/or supporting edges, is optionally selected from a set of different bladders, based on imaging a subject's body.

Insertion of the Bladder into a Body

In some embodiments, the inflatable bladder is configured in the deflated state by rolling the bladder, as will be described in more detail below with reference to FIGS. 1C, 3A, 3D-3G.

In some embodiments the bladder is rolled into a thin shape for inserting through a small hole. The diameter of the rolled shape may be about 1-10 mm, optionally 2-3 mm in diameter, optionally fitting inside a 16 French catheter.

In some embodiments the bladder is rolled as double inwardly rolled wings, as will be further described below with reference to FIGS. 3A and 3D.

In some embodiments the bladder is guided to a target location in a body by an introducer tube.

In some embodiments the introducer tube is connected to the bladder by a rigid connector, optionally a biodegradable connector.

In some embodiments the connector includes a hinge configured to allow relative motion between the introducer tube and the bladder only in desired directions.

In some embodiments the introducer tube is moved toward its target location, at least partly, by a motorized mechanism, as will be described further below with reference to FIG. 8.

In some embodiments, a processor controls the motorized mechanism.

In some embodiments, the processor also controls inflation of the bladder, optionally also controlling lateral expansion and/or thickness of the bladder.

In some embodiments, the processor also interfaces with an imaging system, such as a Trans-Rectal Ultrasound (TRUS), thereby optionally providing an image of the bladder and its location and/or surrounding organs.

Example Methods of Using Embodiments of the Invention

In some embodiments of the invention, the tissue dissecting device described above, and in further detail below, is typically used by inserting the inflatable bladder, in a deflated state, into a slit, a hole or a small space in a body, inflating the bladder to expand, thereby dissecting tissue by the enlarged volume in-between tissue layers.

In some embodiments the dissection occurs while the bladder's leading edge(s) are being pushed against tissue and/or in-between tissues during bladder unrolling.

In some embodiments the dissection happens by an edge of the bladder being pushed against tissue by lateral expansion, and dissecting the tissue.

In some embodiments the dissection happens by sides of the bladder being pushed against tissue when thickness of the bladder is increased, and dissecting the tissue by pulling it apart.

In some embodiments the lateral expansion and/or the thickness of the bladder are limited, thereby avoiding harm to laterally positioned tissues or organs.

In some embodiments the lateral expansion and/or the thickness of the bladder are limited, thus simplifying a job of a practitioner, who does not need to be trained in when to end inflation.

In some embodiments the practitioner inserts the bladder into an existing space in a target location in a body. In some embodiments the practitioner inserts the bladder into a prepared space in a target location in a body, which was prepared surgically, optionally by hydrodissection.

In some embodiments the bladder is specifically shaped in the shape of a desired dissection thus simplifying a job of a practitioner, who does not need to be trained in when to end dissection.

In some embodiments the bladder is guided to a target location by a catheter.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Reference is now made to FIG. 1A, which is a simplified flow chart illustration of a method of tissue dissection according to an example embodiment of the present invention.

FIG. 1A describes a method for dissecting tissue, which includes:

inserting an inflatable bladder, in a deflated state, into a space in a body (5);

inflating the bladder to a substantially planar form (1010), thereby dissecting tissue.

In some embodiments of the invention, the bladder is expanded to a substantially planar form, and further inflation causes dissection.

The present invention, in some embodiments thereof, includes devices, systems and methods which can be used to mechanically dissect and/or separate between adjacent tissues, optionally of different bodily organs. These devices and methods are especially useful in anatomic locations where accurate maneuvering, placement and deployment are important for safety and overall treatment success. In some embodiments, one useful outcome using such means is to protect a first tissue from the effect of treatment conducted on a second and adjacent tissue.

Some embodiments of the present invention include a bladder which is spreadable and/or expandable from a substantially or even fully collapsed form to a partially or fully spread and/or expanded form between two adjacent tissues of a body of a subject (such as a human). Such spreading may be lateral (e.g., sidewise) and/or vertical (e.g., in height). As such, this change in form of the bladder initiates and/or promotes dissection of and/or in-between these adjacent tissues. Optionally, though not necessarily, the bladder further separates these adjacent tissues.

In some embodiments of the invention, pressure is gradually increased, optionally using a syringe to inject fluid, such as, for example, saline, into the bladder. As additional saline volume is introduced, bladder portions which reach maximal thickness extend laterally, optionally until unrolling is complete and bladder fully extends. During such "unrolling extension", a distal, rolled/curved portion of the bladder is pushed against connective tissue and/or inbetween two connected tissue layers. Radial forces are applied towards tissue layers and connective tissue, thereby promoting dissection, tearing and/or separation of the two tissue layers.

Tissues which are described herein as dissected and/or separated, such as "adjacent tissues" or "first tissue" and "second tissue" can denote two tissue types (for example, prostate-rectum, uterus-rectum, uterus-small bowels, urinary bladder-uterus, ovary-bowels uterus-urinary bladder, liver-gallbladder, lung-mediastinum, mediastinum-lung, mammary gland-thoracic wall, esophagus-spine, thyroid-blood vessels, thyroid-pharynx and larynx, small bowels and large bowels-retroperitoneum, kidney-liver, pancreas-stomach, pancreas spine, stomach-liver, stomach-spine, etc.), same tissue type, or different tissue regions of the same tissue type.

It will be appreciated that two tissue regions can be naturally adjacent and attached by fibroconjunctive tissue (e.g., lobes of a lung) and can be dissected and/or separated by the introduction of an incision. In any case, the device of the present invention is designed such that an expanded shape thereof is selected capable of cutting, dividing and/or displacing the first tissue from the second tissue.

In some embodiments, physical dissection and/or separation, optionally combined with a barrier effect of the device, protect the first tissue from an effect of a treatment applied to the second tissue. The treatment, when used in context of the first and second tissues, denotes any treatment to any of the first tissue and second tissue. In some instances the treatment can be harmful to an untreated tissue (e.g. first tissue).

Examples of such "harmful" treatments include radiation treatment, such as, for example, external radiation therapy using gamma irradiation, high energy photon beam therapy, electron beam therapy, proton beam therapy, neutron beam therapy, heavy particle beam therapy, conformal 3d radiation therapy, intensity modulated radiation therapy (IMRT), ionizing radiation, or non-ionizing radiation (microwave therapy, radiofrequency therapy, high intensity focused ultrasound therapy, etc), or interstitial therapy such as, for example, interstitial brachytherapy, interstitial thermal ablation, contact thermal ablation by hot liquid, high intensity focused ultrasound, thermoregulated rods, interstitial laser therapy with or without photodynamic agents, cryotherapy, interstitial chemical ablation, localized chemotherapy, or any combination thereof. Treatment can also include drug treatment (local) such as alcohol tissue ablation or hyperosmolar ablation using NaCl crystals or hyperosmolar solution or physical tissue manipulation (e.g. separation).

Such a device may be useful in invasive treatments, such as, surgical extirpation, when blunt dissection and/or separation of tissue can be difficult and can result in inadvertent injury to adjacent organs. Another exemplary invasive treatment may be a surgical prolapse repair. It will be appreciated that any number of the present device can be utilized to fill complex spaces in order to displace one tissue from another. The devices might be interconnected in order to maintain a functional protective structure. Multi-device structures might be suitable for physical dissecting and/or separating adjacent tissues in the peritoneal cavity wherein some of the interconnected devices serve as anchors to the body wall preventing movement and migration of the structure.

In some embodiments of the present invention a tissue dissection device is used for tissue dissection and tissue reinforcement. Examples of tissues which may be reinforced include, but are not limited to, abdominal cavity wall, diaphragm, and pelvis. Such weak regions may be represented, but without limitation, by abdominal wall weakness such as hernia, or weakness of vaginal walls such as anterior vaginal wall prolapse, posterior vaginal wall prolapse, uterine or vaginal cuff prolapse, and urinary incontinence by hypermobility of urethra. In an exemplary use, a device of the present invention is introduced to a desired location adjacent to weakened tissue, such as but not limited to, between the fascia and skin, or between the fascia and the peritoneum, and inflated under direct vision or another imaging method such as ultrasound, Laparoscopy (visual), CT or MRI. In some embodiments, such device may comprise an inflatable, possibly biodegradable dissecting portion, and a tissue reinforcing component such as a non-biodegradable mesh.

In some embodiments of the invention a tissue dissection device is used to help removal of tissue (like a gall bladder, uterus).

Example Expandable Devices for Tissue Dissection/Separation

Figure 1B:
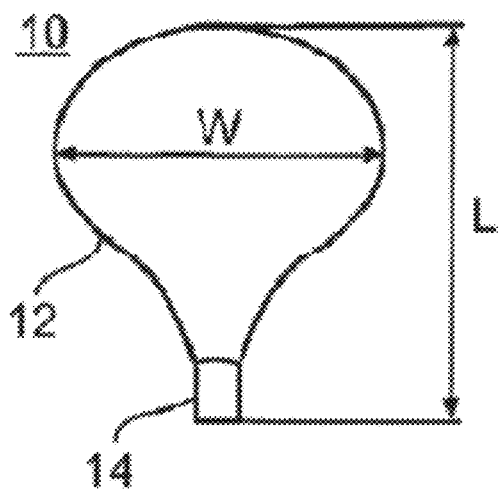
FIGS. 1B-D are simplified illustrations of an inflatable bladder constructed according to an example embodiment of the present invention.
Figure 1C:
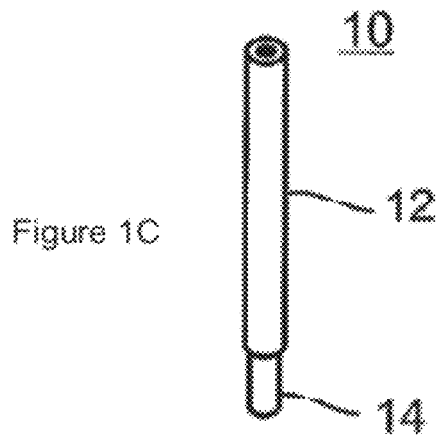
Figure 1D:
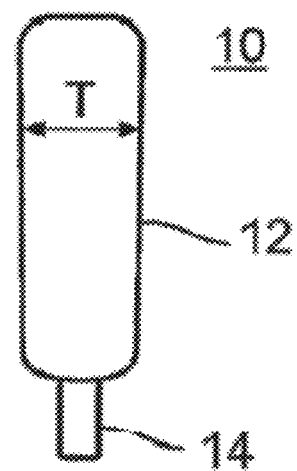

Reference is now made to FIGS. 1B-D, which are simplified illustrations of an inflatable bladder constructed according to an example embodiment of the present invention.

FIGS. 1B-1D illustrate an inflatable bladder which is referred to herein as device 10.

Device 10 includes a bladder 12 which can be constructed out of a biocompatible material. As used herein the term bladder refers to a chamber having an inner volume when expanded and less inner volume when collapsed.

Although FIGS. 1B-1D illustrate a planar balloon shape having an expanded state of length L (FIG. 1B e.g. from 1 to 20 cm), an expanded state of width W (FIG. 1B e.g. from 1 to 20 cm) and an expanded state of thickness T (FIG. 1D e.g. from 1 to 10 cm), it will be appreciated that bladder 12 can be fabricated in any shape suitable for uniform tissue lateral dissection and/or vertical displacement thus minimizing any localized pressure on the tissue.

In some embodiments, bladder 12 is vertically expandable until a certain limit (e.g., predetermined thickness T). Optionally, bladder 12 is further expandable in other directions (e.g., in width W and/or length L) until total expansion limitation or until selectively stopping expansion (e.g., by stopping or canceling the source of expansion). In some embodiments, bladder 12 when fully expanded is substantially uniform in thickness T. In some embodiments, bladder 12 is provided or even deployed in a fully or partially collapsed (e.g., folded or rolled) form and during its expansion it includes a spreading phase, that may be present at the beginning, middle and/or end of total expansion duration.

Figure 1E:
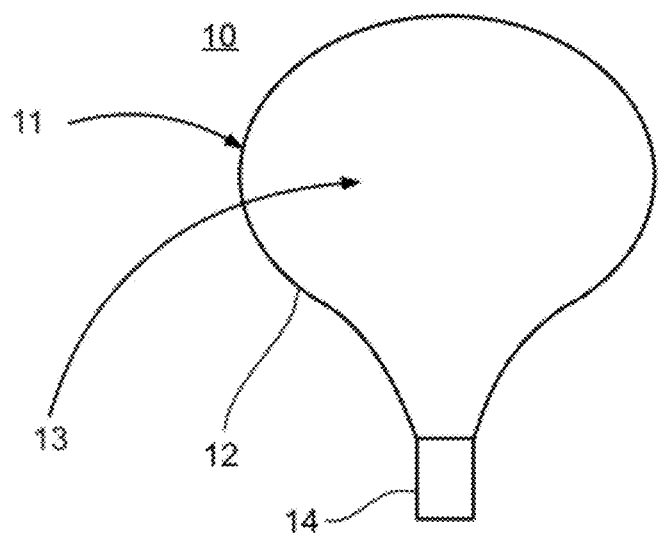
FIGS. 1E and 1F are simplified illustrations of the inflatable bladder of FIG. 1B.
Figure 3A:
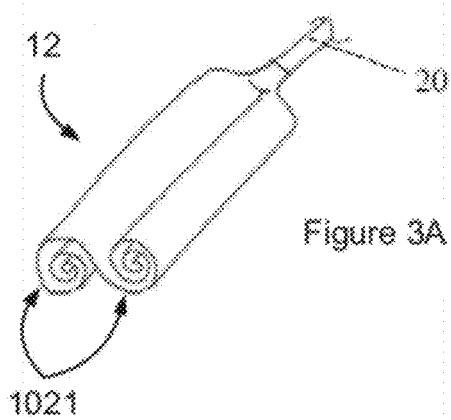
FIGS. 3A-3C are simplified illustrations of an inflatable bladder in different deployment stages, constructed and operating according to an example embodiment of the present invention.
Figure 3B:
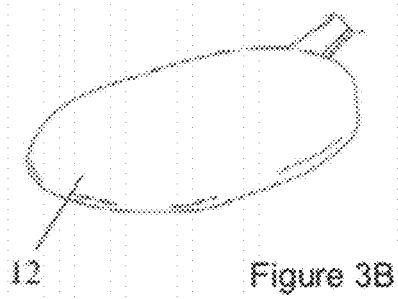
Figure 3C:
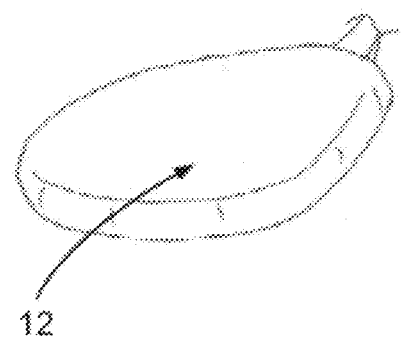

Examples of bladder 12 shapes include, but are not limited to, a pear shape (for example as depicted in FIGS. 1B and 1E), a fusiform shape, a discoid shape, a flattened shape (for example as depicted in FIGS. 1B, 1E, 3B, 3C, 3H-3K, and 3M-3T), a triangular shape (for example as depicted in FIG. 9B), and a flattened cylindrical shape (for example as depicted in FIGS. 3B, and 3C).

Reducing or minimizing localized pressure on displaced tissue can be important since it ensures that displaced tissue is supplied with ample blood flow and thus reducing the chances of localized ischemia. A limit on the pressure is optionally achieved by limiting the bladder from inflating beyond a predetermined pressure, volume and/or thickness.

It will be appreciated that by selecting a shape which enables a limit on pressure on tissue, the some embodiments of the present invention overcome deficiencies balloon-shaped displacement devices, such as described in above-mentioned U.S. Pat. No. 6,852,095, which can generate non-uniform pressure on displaced tissue (in particular soft tissues) and thus can lead to localized ischemia, especially in long term procedures.

In some embodiments, the uniform pressure towards tissue in contact is mostly or solely directed laterally (e.g., sideways) at least during part of expansion phase. In some embodiments, vertically directed pressures are substantially diminished if and once bladder 12 reaches an optional maximal thickness limitation.

Device 10 can be constructed from any biocompatible material including, but not limited to, polymers, such as, biodegradable polyesters made from hydroxyl alkanoic acids, polyorthoesters, polyphosphazenes, polyphosphate esters, polyanhydrides and copolymers and blends thereof. Of particular interest are homo and copolyesters made from lactic acid, glycolic acid and caprolactone. The preferred polymers are those that are in clinical use and have already shown to be safe with predictable biodegradability, i.e. polylactide, poly(lactide-glycolide), poly(lactide caprolactone) and polycaprolactone.

In some embodiments, the inflatable bladder of the device 10 is substantially slippery.

In some embodiments, material constructing the inflatable bladder of the device 10 is substantially slippery.

In some embodiments, the inflatable bladder of the device 10 is coated by a substantially slippery coating.

In some embodiments of the invention the selected polymers should fit the desired mechanical and physical stability of bladder 12 in vivo. A biodegradable polymer which retains its mechanical and physical properties when designed as a thin layer bladder, for at least 2 months is optionally utilized to produce a bladder which needs to retain its mechanical and physical properties for two months in the body. In such embodiments, the polymers may be film forming and flexible enough to enable folding of bladder 12 into a compact configuration which can be inserted within a tube which serves as dispenser for device 10 in vivo.

In some embodiments, material constructing at least a wall portion of the inflatable bladder of the device 10 includes Poly Lactic Acid (PLA) and poly caprolactone. In some embodiments the material includes over 50% PLA. In some embodiments, the material includes 70-90% of PLA and 10-30% of poly caprolactone. In some embodiments, the material includes 70-90% of PLA and at least 10% poly caprolactone.

Exemplary biodegradable devices, inflatable bladders of different shapes, as well as materials and manufacturing thereof are described in details in above-mentioned Published U.S. Patent Application No. 2008/0033471, the disclosure of which is fully incorporated herein by reference.

A device designed capable of such permanent implantation can be particularly useful in cases where a treated individual is subjected to several treatment sessions (e.g., radiation) over an extended time period (e.g. weeks). In such a case, repeated implantation of a tissue protective device and thus repeated discomfort to the individual can be avoided by using an embodiment of device 10 of the present invention.

Expansion of bladder 12 is conducted in place following insertion and positioning of device 10. Such insertion and positioning can be effected by using a guide (a suitable guide is further described hereinbelow with respect to FIG. 2).

Following expansion such a guide can be kept attached to device 10 during short term procedures in which treatment is provided over a course of hours (e.g. thermal ablation) or it can be detached therefrom during longer procedures in which treatment is provided over a course of days, weeks or even months (e.g. long term radiation or interstitial procedures). In the latter case, device 10 is preferably constructed from a biodegradable material such that device 10 degrades and is absorbed in/by the body over a predetermined time period or optionally following absorption of a predetermined dose amount of treatment (e.g., radiation). To enable biodegradation, device 10 is constructed from polymers which are biocompatible and bioabsorbable, and yet posses mechanical properties suitable for adjacent tissue dissection and/or maintaining the desired in-tissue shape.

In some embodiments, device 10 dissects and/or separates one tissue from another when bladder 12 is expanded. Bladder 10 can be expanded using one of several approaches. To enable expansion, device 10 optionally includes a port 14 through which bladder 12 can be expanded and/or collapsed. Port 14 is optionally a small diameter port with a diameter which is ⅕ to ¹/₁₀₀, preferably ⅕ to ¹/₂₀ of the expanded thickness or width of expanded bladder 12.

Port 14 can be a fluid filling port, in which case bladder 12 can be expanded by using gas, liquid or gel and collapsed via emptying. Alternatively, port 14 can be utilized to introduce a solid yet elastic element that can fill bladder 12 such that it assumes a semi rigid expanded state. Bladder 12 can also be filled with beads that can optionally be interconnected by a thread or wire. It will be appreciated that such wire or bead expansion may traverse a need for bladder sealing.

In some embodiments of the invention the port 14 is sealed with a plug which is located inside the bladder. In some embodiments of the invention the plug is detachably connected to a distal end of a catheter/introducer/fluid filling channel, so when the catheter is pulled out, the plug is snugly fitted inside the port 14 lumen. in some embodiments of the invention The plug is eventually disconnected from the catheter while the catheter is ultimately withdrawn. in some embodiments of the invention the plug is made of similar materials to the bladder wall, and/or of biodegradable material.

In the liquid expansion configuration, bladder 12 is preferably constructed from a fluid impermeable material such that an expanded state thereof can be retained following filling. Use of a liquid provides several advantages. It enables bladder 12 to conform to the tissue displaced and thus apply uniform pressure thereupon. It enables introduction of useful agents, such as contrasting agents or treatment agents into bladder 12 and it can serve as an excellent physical barrier against heat, or radiation by introducing substances that absorb radiation such as iodinated agents or fluorocarbons.

Any liquid can be utilized to expand bladder 12, preferably the liquid utilized is biocompatible and physiological such as 0.9% saline, Ringer solution or Hartman solution. The liquid can include agents, such as contrast agents, that can be useful in imaging, radiation and/or thermal treatment modalities.

In some embodiments of the invention, the bladder can leak or sweat or even contain small holes, providing saline and/or slippery material to the dissecting area.

To protect tissue from radiation, agents such as iodinated substances, baritated substances, fluorocarbons, and the like can be included in the liquid. Agents active in tissue healing/repair can also be added to the liquid.

Exemplary Means and Methods of Deploying Expandable Separators

According to another aspect of some embodiments of the present invention, there is provided a system which can be utilized for tissue dissection and/or separation. Such a system includes device 10 and a guide which is detachably attached to device 10. The guide serves to insert and position device 10 and to expand bladder 12 when in position. The guide can be a thin catheter or a blunt tip needle (cannula), of about 1-10 mm in diameter, optionally 2-3 mm in diameter, optionally a 16 French catheter. The guide posses a lumen through which a bladder-expanding fluid (or rigid element) can be conducted from a device such as a syringe (in the case of fluid) to bladder 12. Bladder expansion can be monitored by using different imaging technique such as: direct view, trans-illumination, fluoroscopy, endoscopic or laparoscopic US, US, CT scan, MRI, endoscopic view, etc. The guide is preferably constructed from biomedical grade elastomer such as PVC or polyurethane.

In cases where device 10 is left within the body, the guide is detached from the device 10 which preferably remains inflated by self sealing of port 14. Such self-sealing can be effected by a one-way valve incorporated into port 14, by viscosity of a bladder expanding liquid (e.g. one that forms a gel) or by a biodegradable sealing mechanism such as that described below with respect to FIG. 2. A cutting catheter made from biocompatible material and having a sharp edge may be used to detach device 10 from the guide if necessary.

Figure 1F:
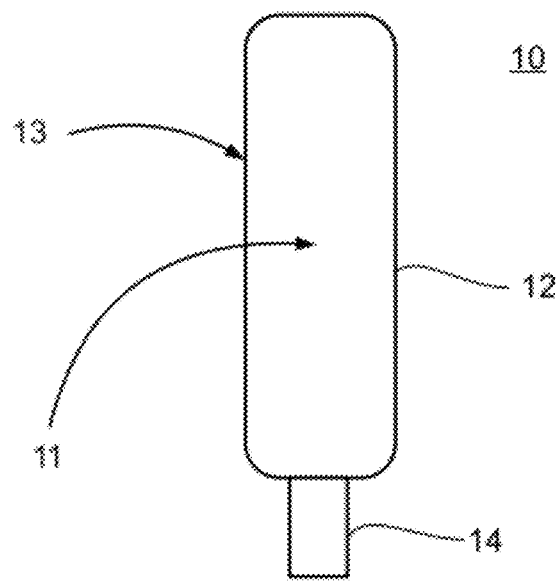

Reference is now made to FIGS. 1E and 1F, which are simplified illustrations of the inflatable bladder 12 of FIG. 1B.

FIGS. 1E and 1F depict the inflatable bladder 12 and the port 14, and depict which regions of the inflatable bladder 12 are referred to as a face 13 (substantially flat regions of the bladder 12), and which regions of the inflatable bladder 12 are referred to as an edge 11 (substantially narrow regions of the bladder, at a perimeter of the bladder).

Figure 1G:
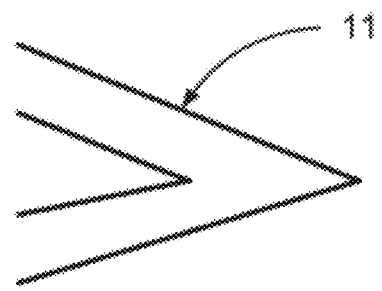
FIGS. 1G and 1H are simplified illustrations of cross sections of a dissecting edge of inflatable bladders constructed according to example embodiments of the present invention.
Figure 1H:
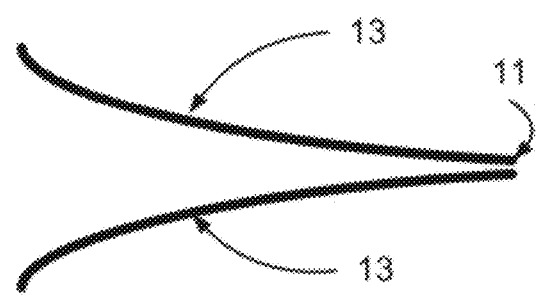

Reference is now made to FIGS. 1G and 1H, which are simplified illustrations of cross sections of a dissecting edge 11 of inflatable bladders constructed according to example embodiments of the present invention;

FIG. 1G depicts an edge 11 which has been produced as a sharp edge.

FIG. 1H depicts an edge 11 which is made sharp by virtue of being produced by two faces 13 being welded or glued at the edge 11. Optionally, a chamfer (not shown) is produced on the edge 13 so as to produce a sharp edge when 11 when the two faces 13 are mated together.

In some embodiments of the invention the stiffened edge is provided support by having a blunt, or rounded, edge on an opposing edge of the bladder 12.

Figure 1I:
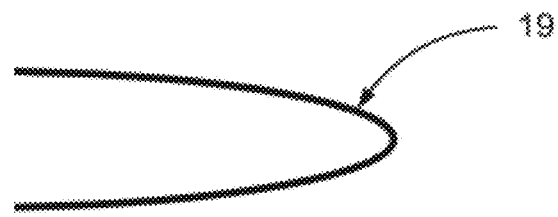
FIGS. 1I and 1J are simplified illustrations of cross sections of a supporting edge of inflatable bladders constructed according to example embodiments of the present invention.
Figure 1J:
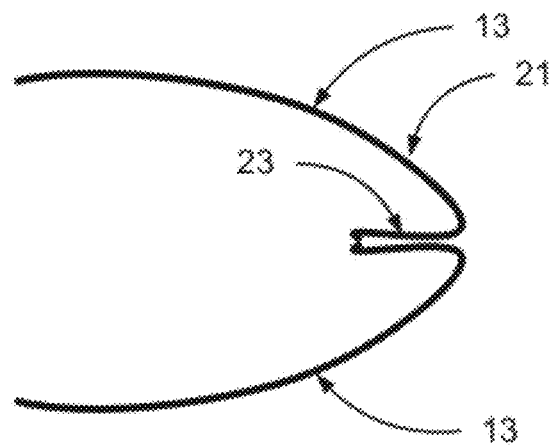

Reference is now made to FIGS. 1I and 1J, which are simplified illustrations of cross sections of a supporting edge of inflatable bladders constructed according to example embodiments of the present invention.

FIG. 1I depicts an edge 19 which has been produced as a rounded edge. The edge 19 is optionally simply a bending of the material used to produce the bladder.

FIG. 1J depicts an edge 21 which is made blunt by virtue of being produced by two faces 13 being bent into the bladder and being welded or glued at a seam 23.

Figure 2:
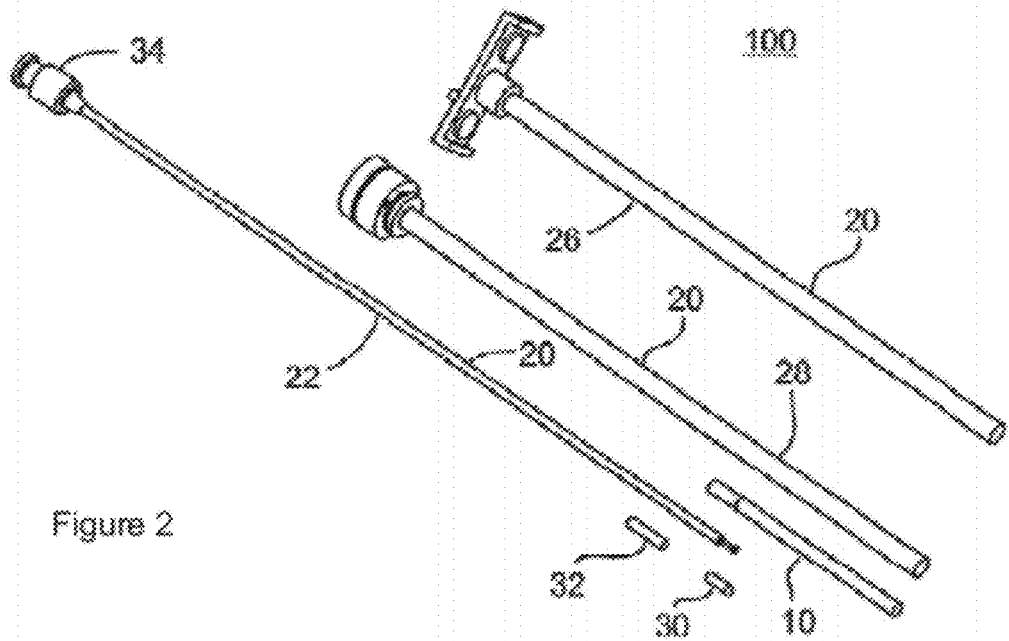
FIG. 2 is a simplified illustration of a device for tissue dissection which includes the inflatable bladder of FIG. 1B and additional parts, constructed according to an example embodiment of the present invention.

Reference is now made to FIG. 2, which is a simplified illustration of a device for tissue dissection which includes the inflatable bladder of FIG. 1B and additional parts, constructed according to an example embodiment of the present invention.

FIG. 2 illustrates an exemplary embodiment of a system for tissue dissection and/or separation which is referred to herein as system 100. System 100 includes device 10 which is shown in a collapsed (rolled) state. System 100 also includes a guide 20 which includes a needle 22 for attaching to port 14 of device 10, a packaging sheath 28 for holding device 10 and a dilator sheath 26 for holding packaging sheath 28. Needle 22 and dilator sheath 26 are used in a manner similar to the well known Seldinger technique (see reference above to "The Seldinger technique", a reprint from Acta Radiologica 1953; AJR Am J Roentgenol. 1984 January; 142(1):5-7). This minimally invasive technique is used to provide a device or substance access to a specific location in the body through a dilator sheath.

Positioning of dilator sheath 26 within a body tissue enables delivery of device 10 (rolled or folded inside packaging sheath 28) to a specific body location. Once positioned, device 10 is optionally deployed by retracting both sheaths and expanding bladder 12 (by, for example, a syringe connected to port 34 of needle 22) at the proper location and orientation. Device 10 is then sealed to prevent deflation by using a one way valve or a self sealing mechanism as described above. Alternatively, port 14 of device 10 can optionally be sealed by using a biodegradable plug 30 which is stuck into a non resilient biodegradable tube 32 attachable at port 14. Alternatively, sealing can be performed by external compression of port 14 with an elastic constricting ring or by knotting of port 14.

When used in long term procedures, needle 22 of guide 20 may be detached from expanded and sealed device 10 and removed from the body, otherwise, following procedure, needle 22 with attached device 10 are removed from the body along with dilator sheath 26 and packaging sheath 28.

Exemplary Means for Compact Delivery and Directional Expansion

Reference is now made to FIGS. 3A-3C, which are simplified illustrations of an inflatable bladder 12 in different deployment stages, constructed and operating according to an example embodiment of the present invention.

In some embodiments, bladder 12 is introduced and/or deployed in a narrow space, optionally between prostate and rectal wall, using guide 20. Bladder 12 may be inserted via or inside a cannula or a protective sleeve (not shown) or maneuvered as-is. In some embodiments, bladder 12 is delivered substantially or fully deflated, optionally folded, optionally as double inwardly folded/rolled wings 1021, either in mirror symmetry (not shown) or anti-symmetrically (e.g., flipped-mirror symmetry; as illustrated in FIG. 3A). In some embodiments, once in-place, bladder 12 is gradually inflated so that at first the inflation promotes unfolding bladder wings, in a specific directional spreading, until a requested/predetermined form is achieved—before or while bladder 12 expands and/or spreads (as illustrated in FIG. 3B). This particular spreading pattern optionally causes lateral dissecting. In some embodiments, when bladder 12 is completely unrolled it is also substantially filled to a maximal and/or predetermined extent. Alternatively, bladder 12 is only partially filled and the treating practitioner may choose to maintain the current inflation state, to further inflate or deflate until a certain chosen degree is met. FIG. 3C shows a substantially fully inflated/expanded state of bladder 12. Optionally, once unfolded, bladder 12 may not be re-folded for example when deflated.

In some embodiments of the invention, the bladder 12 unrolls forward, rather than sideways.

In some embodiments of the invention an edge of the bladder 12 is exposed, and expanding and/or unrolling pushes the edge to dissect.

In some embodiments of the invention, the bladder 12 includes several "fingers" (not shown), each of which expands on its own.

Figure 3D:
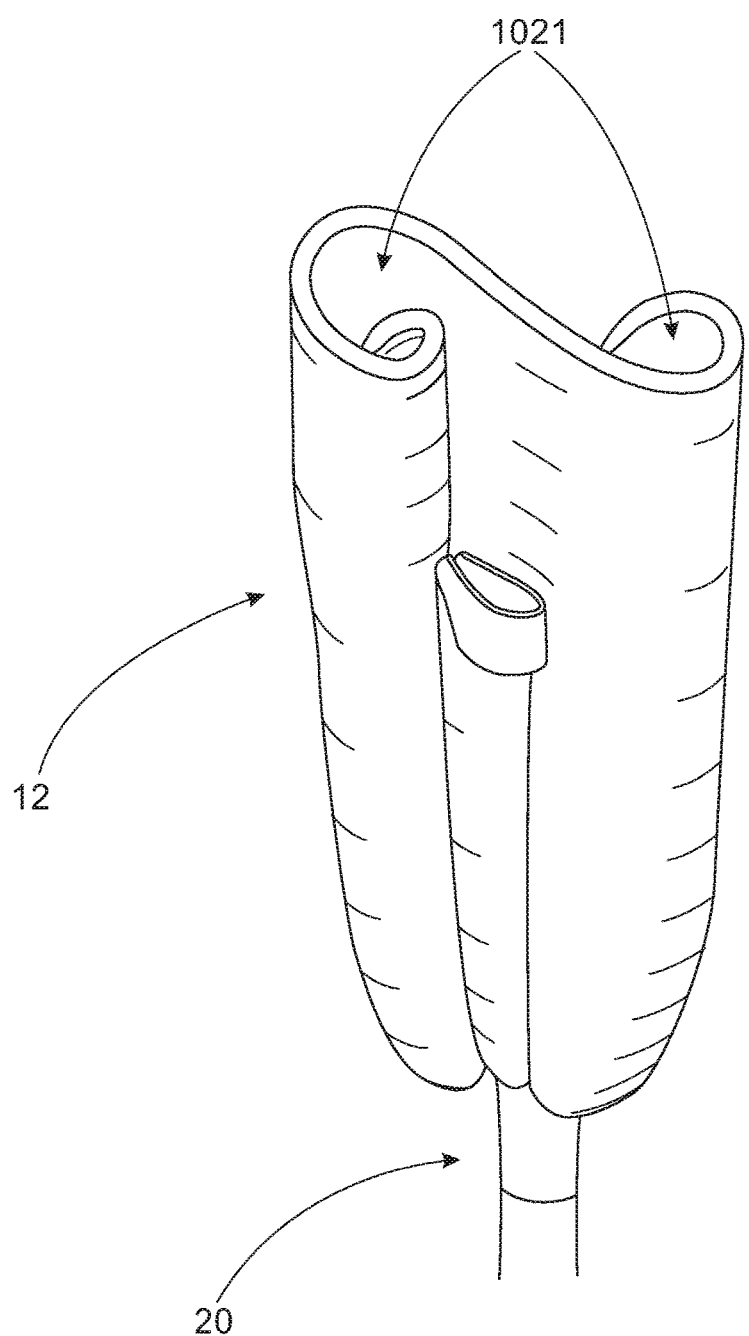
FIG. 3D is a photograph of the inflatable bladder of FIG. 3A.

Reference is now made to FIG. 3D, which is a photograph of the inflatable bladder of FIG. 3A.

The photograph of FIG. 3D depicts the guide 20 and the bladder 12 and the double inwardly folded/rolled wings 1021.

Figure 3E:
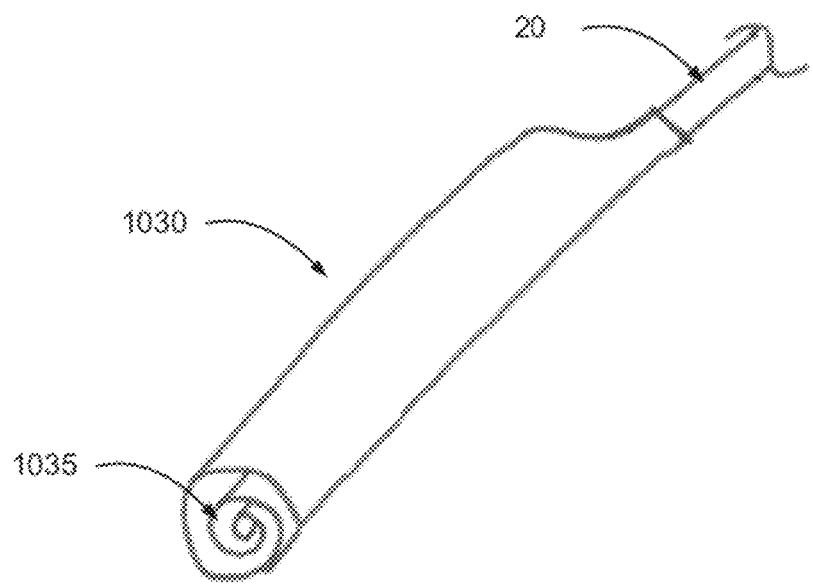
FIGS. 3E-3G are simplified illustrations of alternative embodiments of the inflatable bladder of FIG. 3A, constructed and operating according to example embodiments of the present invention.
Figure 3F:
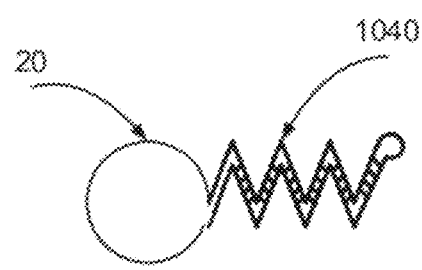
Figure 3G:
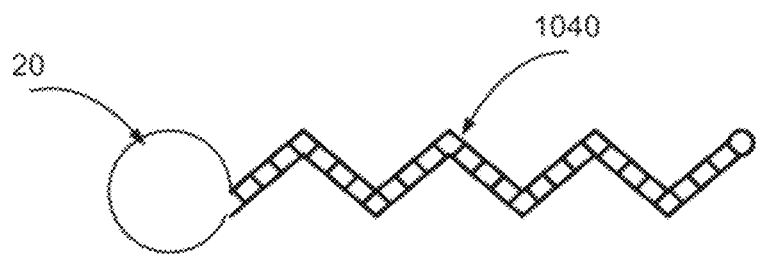

Reference is now made to FIGS. 3E-3G, which are simplified illustrations of alternative embodiments of the inflatable bladder of FIG. 3A, constructed and operating according to example embodiments of the present invention.

FIG. 3E depicts the guide 20 and an alternative embodiment of a bladder 1030, the bladder 1030 being rolled in a single roll wing 1035.

FIG. 3F depicts a cross section of the guide 20 and an alternative embodiment of a bladder 1040 folded, by way of a non-limiting example, in a concertina-like fashion.

FIG. 3G depicts a cross section of the guide 20 and the alternative embodiment of the bladder 1040 of FIG. 3F, somewhat inflated and expanded, to illustrate the expansion of the bladder 1040.

Reference is now made to FIGS. 3H-3K, which are simplified illustrations of an alternative embodiment of an inflatable bladder 1050, constructed and operating according to an example embodiment of the present invention.

FIGS. 3H-3K are intended to depict an embodiment which limits thickness of the inflatable bladder 1050 by having a central hole 1055. The bladder 1050 has a substantially toroidal shape.

Figure 3K:
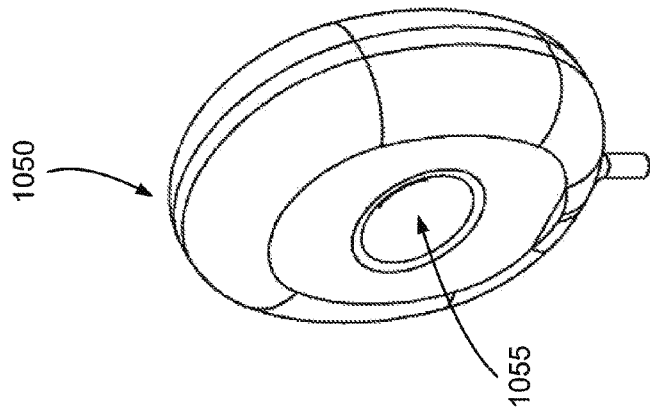
FIGS. 3H-3K are simplified illustrations of an alternative embodiment of an inflatable bladder, constructed and operating according to an example embodiment of the present invention.
Figure 3I:
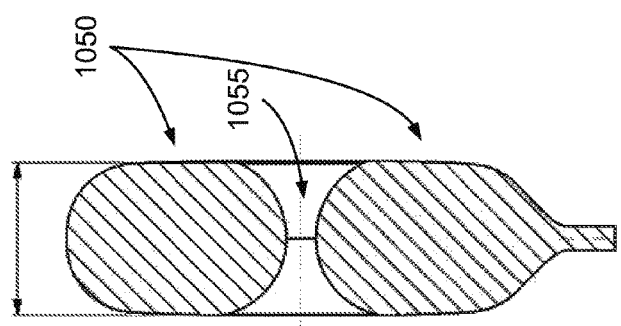
Figure 3H:
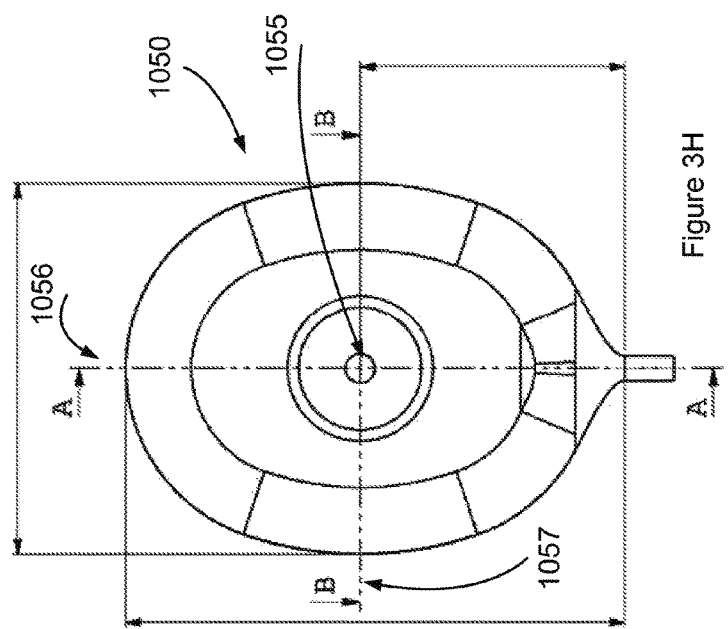
Figure 3J:
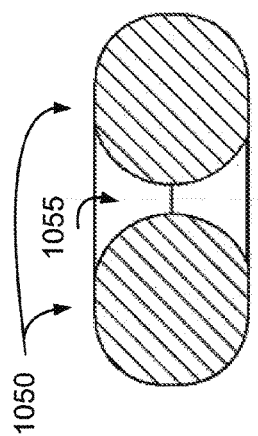

FIG. 3H is a top view of the bladder 1050, FIG. 3I is a cross section of line A-A 1056 of FIG. 3H, FIG. 3J is a cross section of line B-B 1057 of FIG. 3H, and FIG. 3K is an isometric view of the bladder 1050 of FIG. 3H.

Figure 3L:
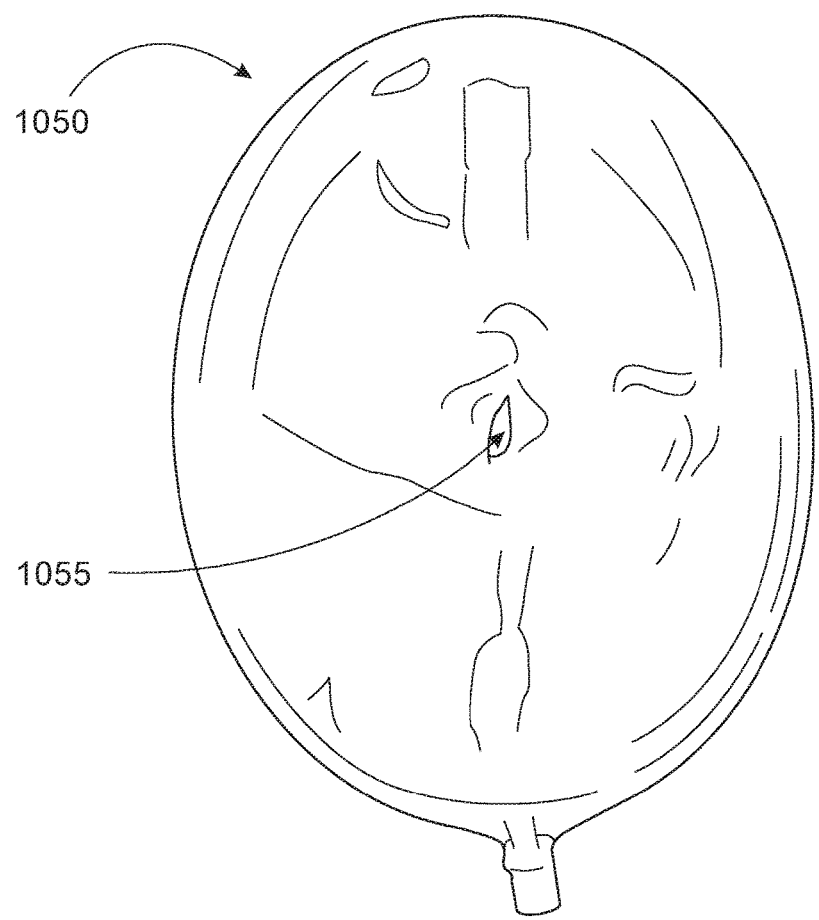
FIG. 3L is a photograph of the inflatable bladder of FIG. 3H.

Reference is now made to FIG. 3L, which is a photograph of the inflatable bladder 1050 of FIG. 3H;

FIG. 3L is a top view of the bladder 1050, also showing the hole 1055 of FIG. 3H.

Reference is now made to FIGS. 3M-3P, which are simplified illustrations of alternative embodiments of an inflatable bladder 1060, constructed and operating according to an example embodiment of the present invention, and to FIG. 3Q, which is a simplified illustration of a 3D model of the inflatable bladder 1060 of FIGS. 3M-3P;

FIGS. 3M-3O are intended to depict an embodiment which limits thickness of the inflatable bladder 1060 by having several holes 1065. The bladder 1060 has a substantially rectangular shape, optionally having rounded corners.

FIG. 3M is a top view of the bladder 1060, showing the holes 1065 and a guide 20, FIG. 3N is a side view of the bladder 1060 and the guide 20 of FIG. 3M, FIG. 3O is another side view of the bladder 1060, FIG. 3P is an enlarged view of area B 1066 and the guide 20 of FIG. 3N, and FIG. 3Q is an isometric view of the bladder 1060 of FIG. 3L.

In some medical applications, support and/or strengthening is provided to tissues, such as in cases of prolapsed organs (e.g., Pelvic organ prolapse). In some embodiments of the invention, a dissection is performed using a dissecting device embodiment, and an implant, optionally a mesh or cloth element, is introduced in-place for tissue support and/or reinforcing. Some embodiments of the invention are configured for combining dissecting and reinforcing in a sequential manner, and some embodiments of the invention are configured for combining dissecting and reinforcing in a simultaneous manner.

Figure 3R:
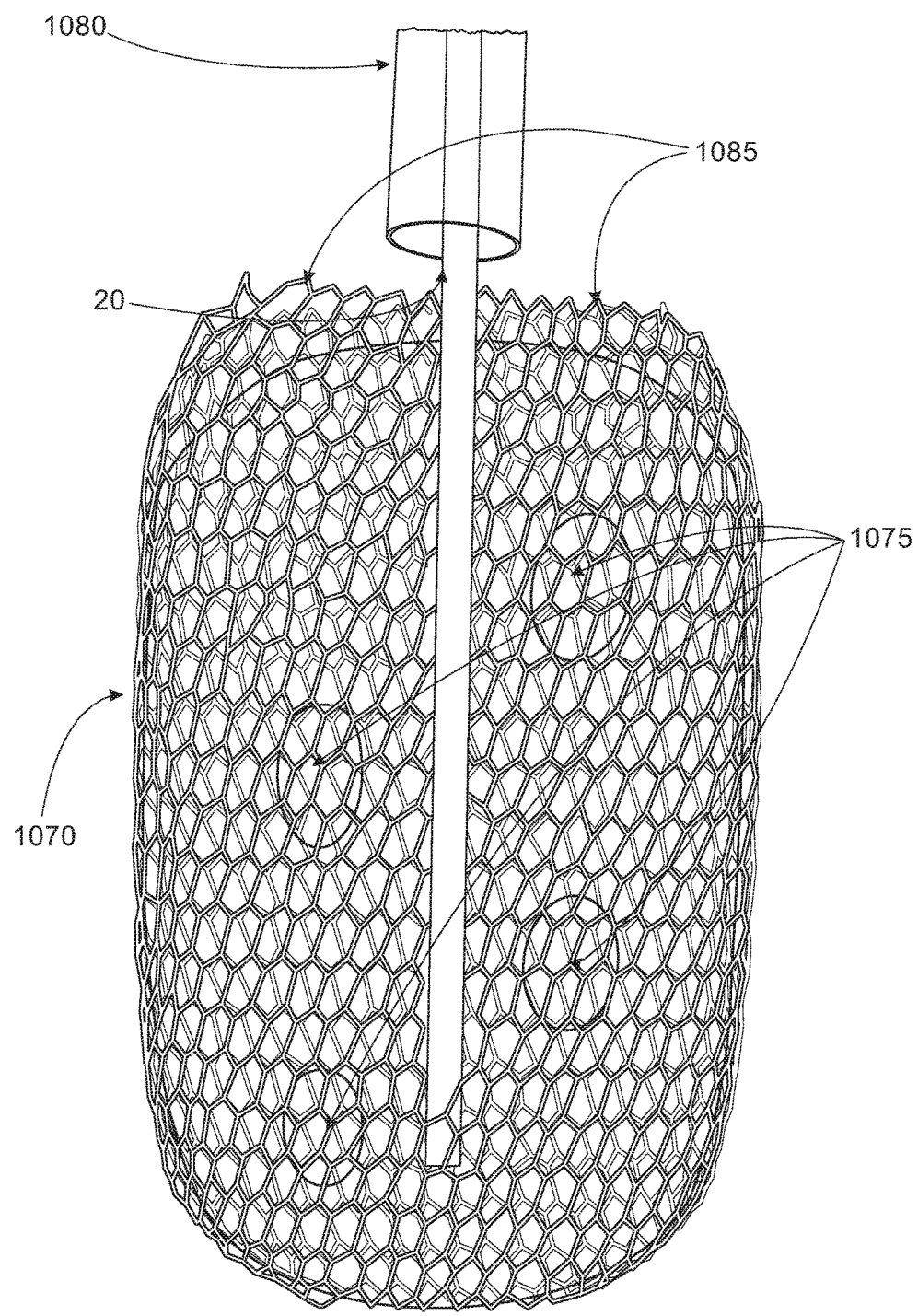
FIG. 3R is a photograph of an alternative embodiment of an inflatable bladder constructed and operating according to an example embodiment of the present invention.

Reference is now made to FIG. 3R, which is a photograph of an alternative embodiment of an inflatable bladder 1070 constructed and operating according to an example embodiment of the present invention.

FIG. 3R is a top view of the bladder 1070, showing holes 1075 and a guide 20. The guide 20 is depicted within an introducer tube 1080. An additional, optional, feature of the bladder 1070 is an attached mesh 1085, which in some embodiments is used for long-term tissue support and/or reinforcing.

In some embodiments, unrolling of the bladder 1070 accommodates deploying and/or centering mesh 1085.

In some embodiments of the invention the mesh 1085 is intended to remain within the body, optionally even adhering onto surrounding tissue and optionally providing support for an organ to which it attaches.

The mesh 1085 is optionally folded with the bladder 1070, attached to the bladder.

In some embodiments, the bladder 1070 is biodegradable, and the mesh 1085 is not biodegradable, so the mesh 1085 remains in the body after the bladder 1070 biodegrades, acting as a permanent tissue reinforcer.

It is noted that the mesh 1085 can be provided with other designs of the inflatable bladder, and is depicted in FIG. 3R as an example.

Figure 3S:
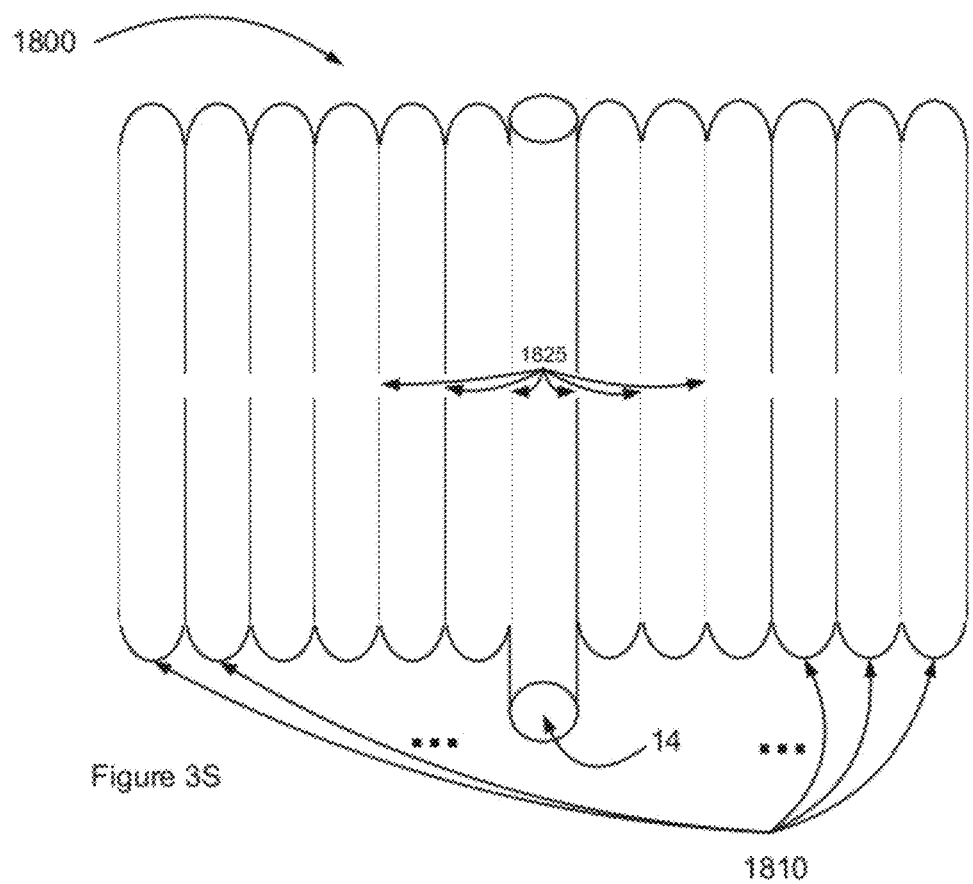
FIGS. 3S and 3T are simplified illustrations of alternative embodiments of an inflatable bladder, constructed and operating according to an example embodiment of the present invention.
Figure 3T:
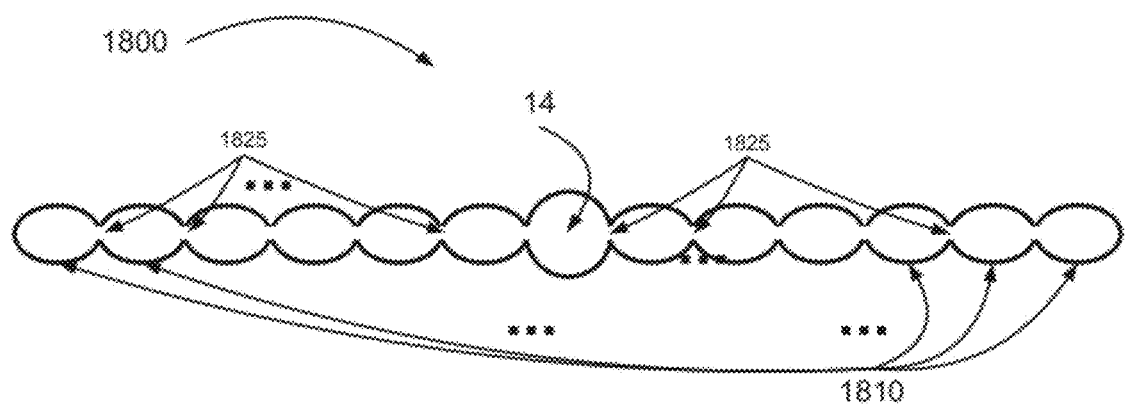

Reference is now made to FIGS. 3S and 3T, which are simplified illustrations of alternative embodiments of an inflatable bladder 1800, constructed and operating according to an example embodiment of the present invention.

FIG. 3S depicts a top view of an inflatable bladder 1800, constructed of parallel inflatable tubes 1810, interconnected by holes, or apertures 1825, enabling inflating material to pass through the apertures 1825 from one inflatable tube 1810 to another. Also shown is a port 14 through which the inflating material can be introduced into the inflatable bladder 1800.

FIG. 3T depicts a cross section view of the inflatable bladder 1800, the parallel inflatable tubes 1810, the apertures 1825, and the port 14.

Exemplary Separating Devices Incorporating Internal Expansion Restrictors

Figure 4:
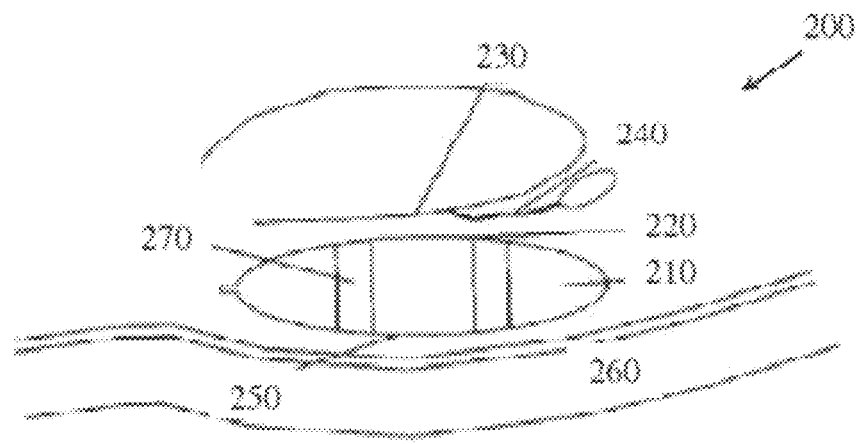
FIG. 4 is a simplified illustration of a cross section of an inflatable bladder in a body, constructed and operating according to an example embodiment of the present invention.

Reference is now made to FIG. 4, which is a simplified illustration of a cross section of an inflatable bladder in a body, constructed and operating according to an example embodiment of the present invention.

FIG. 4 depicts a controllably expandable dissecting system 200 which may or may not be similar in some respects to system 100. In some embodiments, system 200 includes a bladder or inflatable chamber 210, having a generally flattened shape, with a contour that may be but not limited to: round, oval, pear shaped, triangular, or other. Inflatable chamber 210 is shown in a partial inflated/deployed state. In a fully deployed state, the superior surface 220 of the inflatable chamber 210 is configured to be in contact with the inferior-surface of the prostate 230 and the base of the seminal vesicles 240. Alternatively or additionally, in same scenario, the inferior surface 250 of the inflatable chamber 210 is to be in contact with the anterior surface of the rectum 260.

In some embodiments, inflatable chamber 210 is provided with support, to prevent exertion of excessive pressure on the rectal wall during inflation and/or to limit its maximal operational height/thickness and/or to apply directional expansion/spreading in at least one chosen axis, and most preferably two-dimensional lateral spreading (in both width and length). Alternatively or additionally, such or similar means are applied for a lateral spreading/expansion that is preferably controllable, uniform and/or axisymmetric during at least part of spreading/expansion duration. In some embodiments, such a directional or lateral expansion progresses and even reached a finalized or chosen size and/or shape unconditionally to possible resistive forces/pressures.

In some embodiments, inflatable chamber 210 includes longitudinal strips 270 made of non, less or equally stretchable material or designated properties (than for example with respect to a wall portion of inflatable chamber 210), connecting the superior and inferior surfaces of the inflatable chamber positioned at a few mm to 2 cm distance, or preferentially at 1 to 1.5 cm from one another. The length of such strips should be from a few millimeters and up to 2 cm, optionally from 1 to 1.5 cm. Such strips are configured to maintain a maximal chosen height of inflatable chamber 210 (i.e., limitation to vertical expansion) which is determined by the length of a fully extended strip. The forces exercised by the inflatable chamber during and after inflation can optionally be directed laterally in order to dissect and/or create a requested space between the prostate and rectum, while minimizing stresses to the rectal wall.

In some embodiments, vertical expansion is limited by at least one, and more preferably, a plurality of welded, fastened and/or glued dots, lines and/or surfaces, connecting inferior and posterior surfaces of inflatable chamber 210.

Optionally, such limitation means include at least one passage traveling between a first opening and second opening respectively located over posterior and anterior surfaces of inflatable chamber 210.

Figure 5:
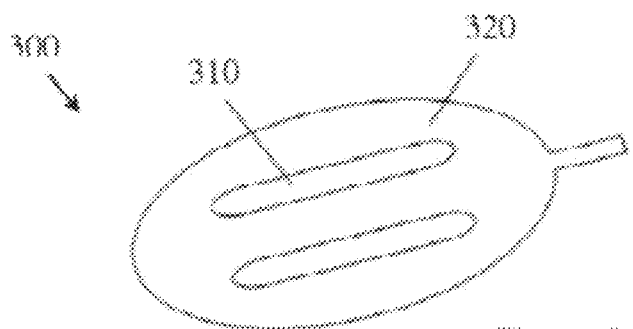
FIG. 5 is a simplified illustration of an inflatable bladder having a portion of one surface of the bladder connected to a second surface of the bladder, according to an example embodiment of the present invention.

Reference is now made to FIG. 5, which is a simplified illustration of an inflatable bladder having a portion of one surface of the bladder connected to a second surface of the bladder, according to an example embodiment of the present invention.

FIG. 5 depicts an inflatable chamber 300 which is provided with at least one passage 310 extending between superior and inferior surfaces thereof. These passages may delineate between them inflatable spaces such as narrow inflatable columns 320, optionally having a diameter of a few millimeters to 1.5 cm when fully inflated. Such columns may optionally be positionable along the longitudinal direction of the prostate. Inflatable chamber 300 can be manufactured of a minimally distensible material and/or having designated columns diameters that may determine vertical expansion limitation.

Manufacturing materials of at least one part of system 200 and inflatable chamber 300 may include any of polyurethane, Nylon, polyester and polyethylene. In case that such a balloon is left implanted and sealed for a longer time, it may be manufactured from biodegradable materials such as but not limited to any of polycaprolactone, PLA, PLGA and polydiaxone.

In some embodiments of the invention, thickness of the material making up the bladder wall is 10 to 1000 microns, In some embodiments 50 to 500 microns, In some embodiments 100 to 200 microns, In some embodiments about 170 microns.

In some embodiments the thickness is substantially constant.

In some embodiments the thickness is non-uniform, to support directional expansion, unrolling, and order of expansion and/or unrolling.

Manufacturing inflatable chambers of the present invention may include a phase of dipping using the disappearing core technology. When strips 270 are applied they may be attached to a sharp metal strip and pulled through the disappearing core and left attached to its superior and inferior surface. During the dipping phase, the disappearing core, the extremities of the strip attached to the surface of the disappearing core may be incorporated within the coating of the core. After dissolving or melting the disappearing core, the strips will be left within the inflatable chamber being attached to the surfaces of the balloon. The disappearing core technology may be applied also for manufacturing devices such as inflatable chamber 300. More information on manufacturing techniques, including but not limited to dipping techniques, may be found in above-referenced PCT Published Patent application number WO/2006/001009, the disclosure of which is fully incorporated herein by reference.

Exemplary External Restrictors

Figure 6A:
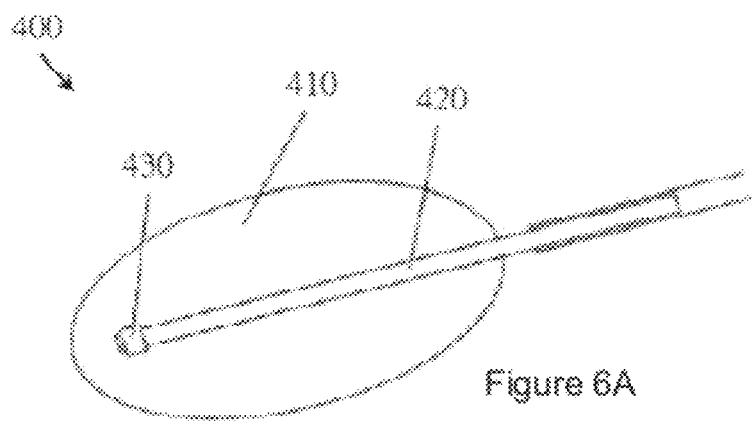
FIG. 6A is a simplified illustration of an inflatable bladder including an external restrictor according to an example embodiment of the present invention.

Reference is now made to FIG. 6A, which is a simplified illustration of an inflatable bladder including an external restrictor according to an example embodiment of the present invention.

FIG. 6A depicts a separator system 400 comprising a separating balloon 410, which is provided with a local external restrictor 420 that is used, at least when selectively deployed, to locally restrict or resist relative movements between system 400 parts and/or natural expansion of adjacent balloon portion in at least one axis. Optionally, when balloon 410 is deployed between prostate and rectum tissues, external restrictor 420 is normally situated on the superior surface of balloon 410, optionally along its longitudinal axis, facing the prostate. The external restrictor 420 optionally or restricts lateral displacement and/or expansion of the balloon, in the direction of the external restrictor 420, during inflation. This optionally provides a limit to the balloon inflating and placing pressure on, one side or another.

It is noted that some embodiments of the invention may use a pair of restrictors (not shown) or more.

External restrictor 420 may be releasably connected to the introducer kit or system, such as by a rigid or semi-rigid strip or rod 430. External restrictor 420 may comprise a ring, tube, groove or projection which is engageable with rod 430. During inflation, rod 430 will prevent lateral displacement and/or unilateral expansion of balloon 410 along part or its entire length. After inflation, the introducer (optionally guide 20 of FIG. 2) is removed and rod 430 is detached from external restrictor 420. In some embodiments, external restrictor 420 is permanently connected or is an integral member of balloon 410. In case where balloon 410 comprises biodegradable materials, external restrictor 420 may be manufactured of same or similar materials, biodegradable or non-biodegradable.

In some embodiments of the invention the restrictor 420 substantially restricts lateral movement of the balloon 410.

Figure 6B:
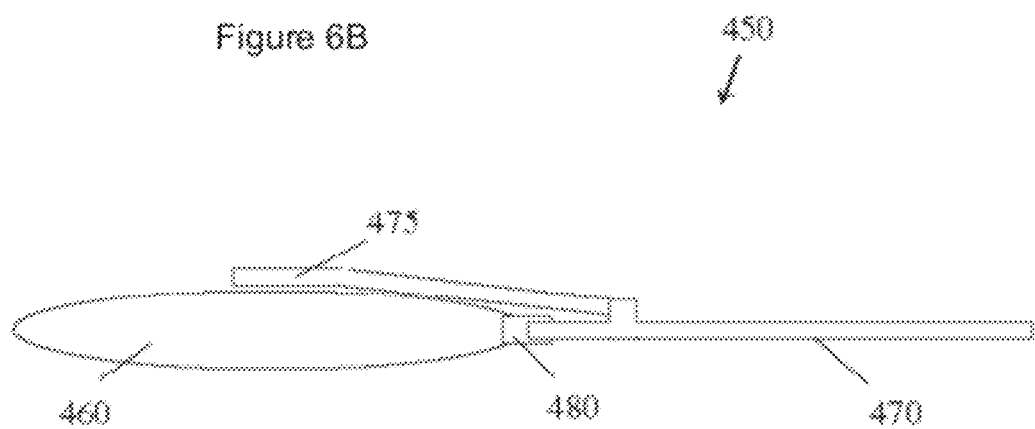
FIG. 6B is a simplified illustration of an inflatable bladder including a guide member according to an example embodiment of the present invention.

Reference is now made to FIG. 6B, which is a simplified illustration of an inflatable bladder including a guide member according to an example embodiment of the present invention.

FIG. 6B depicts a system 450 comprising a separating balloon 460, which may be generally similar in design, shape and/or forming materials to any of the previously described inflatable devices. In some embodiments, system 450 further comprising a guide member 470 releasably attached to balloon 460 via port 480. In some embodiments, guide member 470 includes a lumen traveling therethrough (not shown) which serves as an inflation lumen, which is direct communication with port 480, now serving also as balloon 460 inflation port. In some embodiments, guide member 470 comprises a distal extension 475 that travels over part of balloon 460 length. Extension 475 may be an integral extension of guide member 470 or a differentiated part connected to it, permanently or detachably. Extension 475 may be rigid or elastic, optionally made of biocompatible steel/alloy that is configured to externally restrict/resist tridimensional expansion and/or lateral displacement of balloon 460 away from the position of extension 475. Optionally, extension 475 is not coupled at its distal end and/or not coupled to any portion of balloon 460. In some embodiments, extension 475 allows accurate placement and/or deployment of balloon 460 in a chosen location and arrangement between prostate and rectum tissues, and may be withdrawn (following guide member 470 release from port 480) after deployment and inflation of balloon 460.

In a preferred embodiment, FIG. 12, the balloon 1031, is provided with a non-displacement means 1032, necessary during inflation. Such means 1032 should be preferentially situated on the superior surface facing the prostate in the middle of the balloon and should prevent lateral displacement of the balloon during inflation. This may be necessary since the balloon is flattened and may inflate to one side or another. Such means may be releasably connected to a means within the introducer kit or system such as a rigid or semi-rigid rod or strip 1033. During inflation means 1033 will prevent lateral displacement of the balloon. After completing the inflation, the introducer is removed and the means 1033 is detached from means 1032. In case of a biodegradable balloon means 1032 may be manufactured of the same material as the balloon and may consist of a ring, tube, grove or projection that is engaging the means 1033 from the introducer kit.

Exemplary Over-the-Wire Placement

Figure 6C:
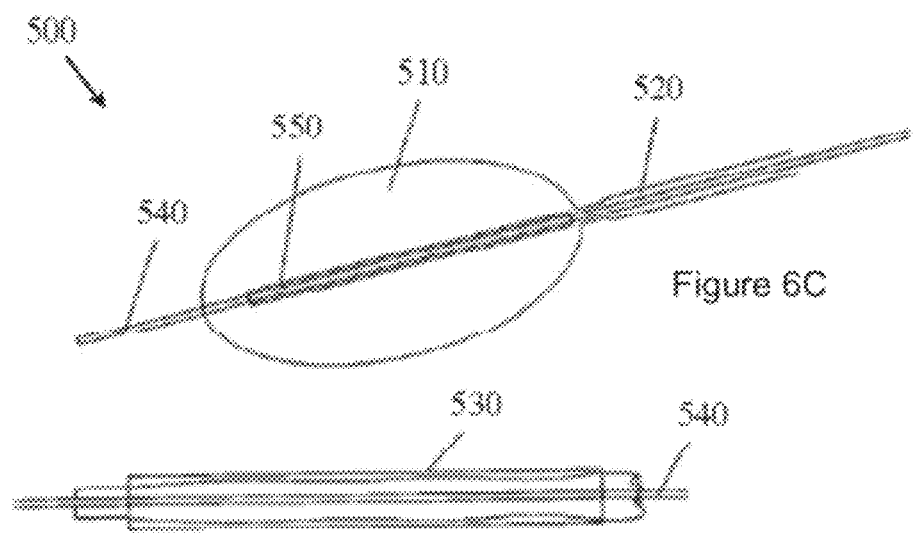
FIG. 6C is a simplified illustration of an inflatable bladder depicting over-a-wire placement according to an example embodiment of the present invention.

Reference is now made to FIG. 6C, which is a simplified illustration of an inflatable bladder depicting over-a-wire placement according to an example embodiment of the present invention.

FIG. 6C depicts a tissue separator 500 comprising a balloon 510 which is provided with height limitation during inflation as mentioned in at least one of previous embodiments related to FIGS. 4 and 5.

The device may be provided with an inflation tube 520. The device may be folded to a minimal diameter within a sheath 530 and may be introduced directly within tissue or through an introducer sheath. A needle or guide wire 540 may be used for directing the device in place. Needle or guide wire 540 may pass between the folds of the folded device or through a dedicated channel 550 passing through balloon 510. Channel 550 may also serve to prevent lateral displacement during inflation when the guiding needle is left in place during inflation or when using a stiff guide wire during such inflation.

Figure 7:
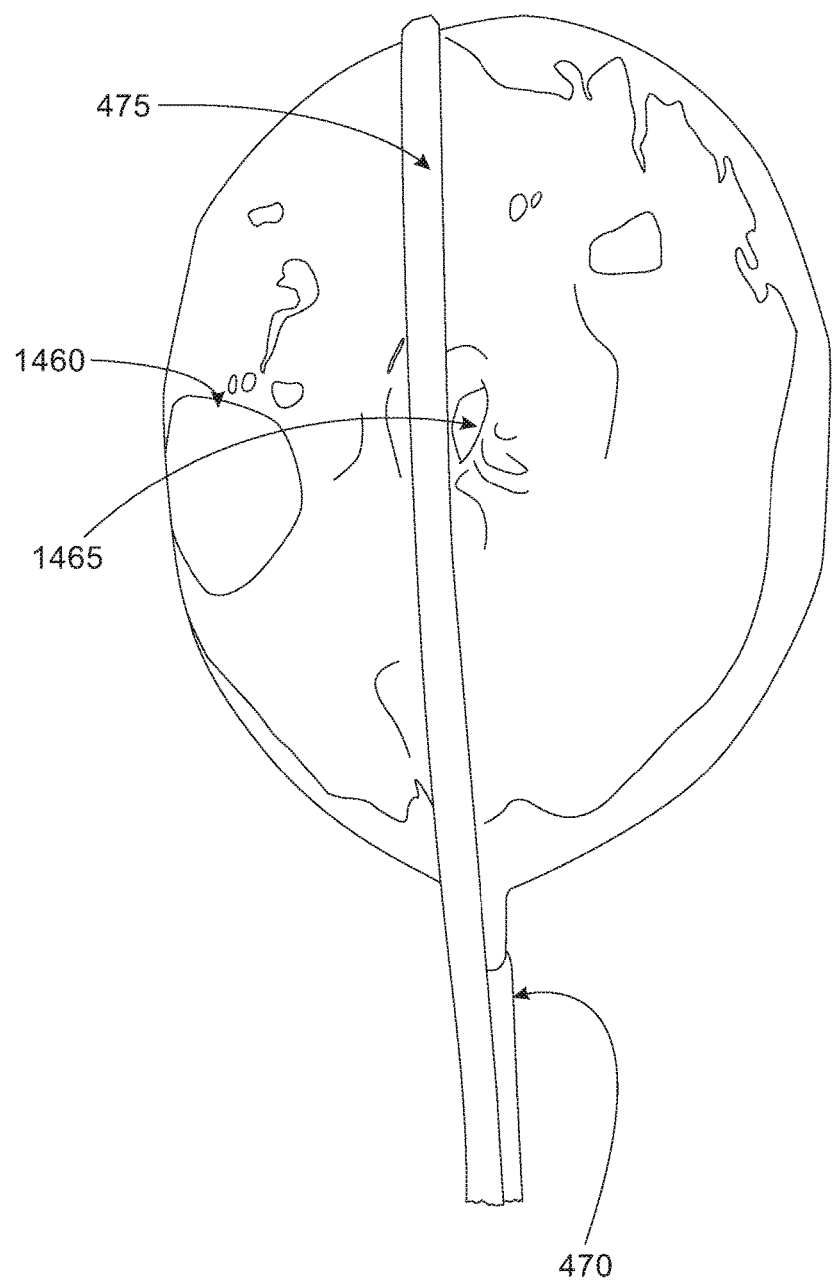
FIG. 7 is a photograph of a system similar to the system of FIG. 6B.

Reference is now made to FIG. 7, which is a photograph of a system similar to the system 450 of FIG. 6B.

FIG. 7 depicts a separating balloon 1460 similar to the separating balloon 460 of FIG. 6B, yet having a central hole 1465; a guide member 470 similar to the guide member 470 of FIG. 6B; and an extension 475 similar to the extension 475 of FIG. 6B.

Exemplary Guiding System

Figure 8:
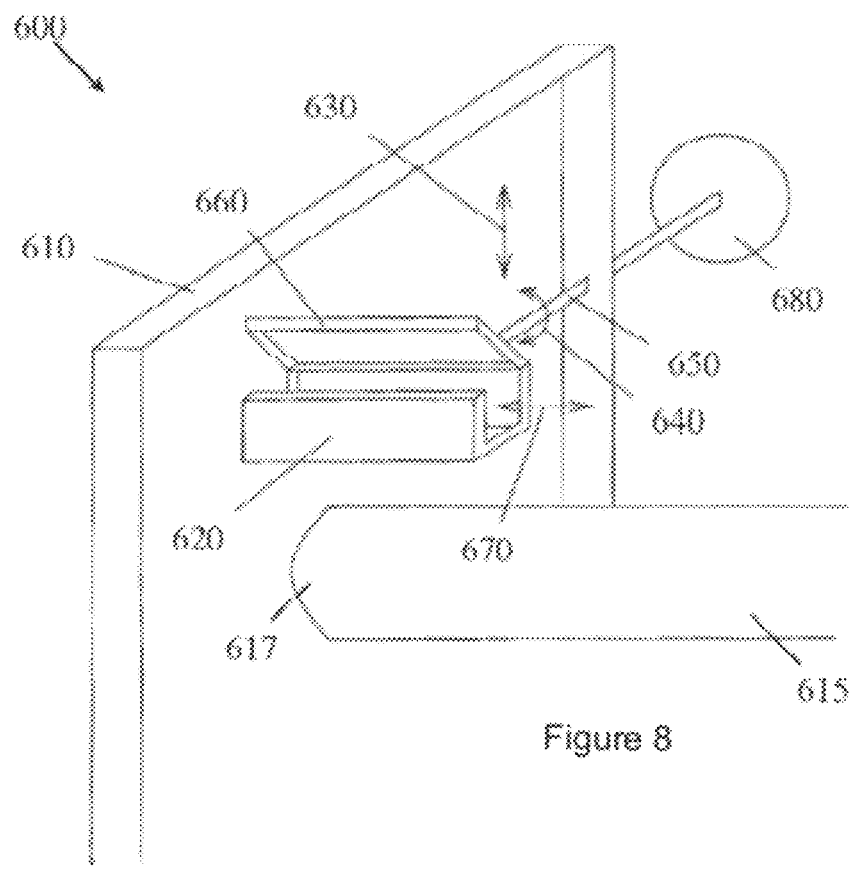
FIG. 8 is a simplified illustration of a motorized mechanism and a Trans-Rectal Ultrasound (TRUS) probe according to an example embodiment of the present invention.

Reference is now made to FIG. 8, which is a simplified illustration of a motorized mechanism and a Trans-Rectal Ultrasound (TRUS) probe according to an example embodiment of the present invention.

FIG. 8 depicts a guiding system 600 comprising a frame 610, which is mounted on a stepper motor 615 coupled with an imaging probe 617. In some embodiments, probe 617 is a TRUS probe. Guiding means 620 which may consist of one or more rigid tubes and or grooves is attached to frame 610, which are movable relative to frame 610 in one or more directions 630 and may be angled relative to the frame in one or more planes 640 using dedicated hinges or grooves 650. In some embodiments, system 600 is part of a robotic system, or connectable to a robotic system or controlling processor (not shown), which includes autonomous, semi-autonomous and/or manual operational modes.

In some embodiments, guiding means 620 are situated in the midline and may be moved in the perpendicular direction relative to the TRUS stepper or cradle. This way, guiding means 620 may be angulated in the sagital or longitudinal plane. In such a formation, guiding system 600 allows maneuverable introduction of an inflatable device into the space between the prostate and rectum, through the perineum, at a chosen/proper height and angle. Guiding means 620 may be provided with coupling means 660 releasably attached to an inflatable chamber introducer, such as but not limited to flaps or covers provided with hinges. This kind of attachment means may be necessary in case that the introducer has to be released from guiding means 620 in a direction lateral or perpendicular to a direction 670 in which the introducer is advanced.

Guiding system 600 may be supported by an electronic guiding system (not shown), which may consist of sensors 680 capable of sensing the translation and rotation of guiding means 620 in respect to frame 610. The retrieved parameters may be analyzed and/or used for calculations by a system of linear equations using standard software languages, defining a line in one plane or in the tridimensional space. The ultrasound (US) image may be displayed on a computer monitor with a superimposed line depicting the expected path of the needle and introducer when advanced through guiding means 620. Additionally, guiding means 620 may be provided with motors 690, such as step motors, which can induce predetermined translations in different directions and angulations in various planes of the guiding means. A desired path may be chosen on the screen on which the US image is depicted by connecting between two points, optionally observable on the monitor.

Such mechanical guiding system with or without the electronic system described may also serve for guiding a diagnostic or therapeutic probe within the body 20 using US or other modalities such as CT, MRI, PET SPECT fluoroscopy, ETC. The advantage of such system is that the imaging modality is fixed and the guiding system is moved in a very accurate way in relation to it in order to access the target. This is especially useful for US probes that are held generally by the operator and manipulated to bring the guiding cursor to the target, a procedure that is inaccurate and cumbersome. Such a system may serve for liver biopsies or introduction of therapeutic probes, abdominal biopsies or introduction of abdominal probes or catheters, or for amniotic aspiration or placental biopsies.

In some embodiments of the invention guidance is provided by the practitioner performing the guiding, via the motorized guidance system. In some embodiments of the invention guidance is provided automatically, via the motorized guidance system.

In some embodiments of the invention a guidance path to the target location is provided by the practitioner performing the guiding. In some embodiments of the invention a guidance path to the target location is provided automatically.

In some embodiments of the invention changes in the relative position of target and catheter are tracked by the practitioner performing the guiding. In some embodiments of the invention changes in the relative position of target and catheter are tracked automatically.

Exemplary Utilization of Expandable Separators in Prostate Treatments

Reference is now made to FIG. 9A, which is a simplified illustration of an example location for using a tissue dissecting device according to an example embodiment of the present invention.

In radical prostatectomy (using either the open or the laparoscopic approach), the device of the present invention is inserted into the space 905 between the rectum and prostate (see FIG. 9A) using the transperineal approach which is guided by transrectal ultrasound. Initially a thin 22 to 18 gauge needle is introduced into this space under trans-rectal ultrasound guidance and this virtual space is enlarged by injecting 5 to 20 cc of physiological liquid such as, for example, 0.9% sterile saline (a process sometimes referred to as "hydrodissection").

In an optional scenario, relevant mostly or solely in radical prostatectomy, a guide wire is inserted through the needle into this space and the needle is removed and a dilator is used to enlarge the tract. In most other scenarios, the needle is kept in body and serves as guiding means instead.

An introducer sheath, optionally a 16 French sized introducer, is passed over the dilator and the dilator and the guide wire or needle are optionally removed; the folded device with its sheath (measuring between 1 and 3 mm in diameter) are introduced through the introducer sheath and the bladder component is deployed and expanded in the space between the rectum and prostate in the proper orientation.

Reference is now made to FIGS. 9B and 9C, which are simplified illustrations of a top view and a side view of an inflatable bladder constructed according to an example embodiment of the present invention.

A flattened pear shaped non distensible bladder 3 to 5 cm length, 3 to 5 cm width and 1 to 2 cm height (see FIGS. 9B and 9C) is optionally used. Upon expansion with either a biodegradable material or physiological solution, the bladder thickness will range between 10 to 20 mm, and optionally limited to a certain predetermined size. A specific bladder size corresponding to the size of the prostate in that particular patient may be used.

Thereafter, an optic fiber can be introduced into the bladder through the needle and the needle can be removed (unless previously removed). During dissection and/or separation of the prostate from the rectum the optional optical fiber can used for illumination and the space between the rectum and prostate may be viewed through a laparoscope by trans-illumination.

Using such an approach, the borders of the prostate can be clearly seen and the prostate can be safely and rapidly dissected/separated from the rectum and from the erectile nerves lying on the rectal side. In such a procedure, the device bladder is optionally filled with a substantially viscous inflation medium (e.g., gel), so a potential puncturing of the bladder wall with a surgical instrument or damage thereto caused by thermal energy will not lead to less efficient outcome. Following the procedure, the bladder and inflation medium are removed using suction and laparoscopic instruments, unless the bladder is applicable and chosen to serve as a long term implant.

In treatments where the bladder is utilized for implantation, such as in prostate irradiation procedures, the device of the present invention is optionally a pear shaped optionally 3 to 5 cm in length, 3 to 5 cm in width and 1-2 cm in thickness when expanded. The bladder is inserted into the correct space between the rectum and prostate as described above under local anesthesia. The bladder is then deployed and filled with physiological liquid or gel to its final dimensions and in the proper orientation.

Optionally, the catheter is then detached from the inflated bladder, and the bladder is sealed in order to prevent deflation. Such sealing may be performed by using a biodegradable plug as described above or by tying of the biodegradable feeding tube. The bladder is sealed for the duration of the radiation therapy thus preventing its collapse.

Patients may undergo 30 to 40 sessions of radiation to the prostate 70 to 84 Gy on an ambulatory basis over a period of 5 to 6 weeks. Therefore, the bladder and/or the inflation medium are chosen in such way so as to degrade following this period of time. Moreover, a radiation barrier in the form of a iodinated substance or fluorocarbons may be introduced into the bladder and/or the gel in order to further reduce exposure of the rectal wall, erectile nerves and bladder base to radiation and therefore permit use of a higher radiation dose (e.g. more than 80 Gy or 8000 rads).

Use of a bladder as described above is provided, for example, by FIG. 4.

A radiotracer can optionally be used in order to enable delineation of the prostate during radiotherapy. The urinary bladder and external urinary sphincters can be additionally protected by using additional spacers on the anterior surface of the prostate at its base and between the sphincter and prostate apex. Moreover, since these spacers compress the prostate and separate adjacent tissues, the respiratory movements of the prostate are reduced permitting a more accurate dose delivery to the prostate.

Some embodiments of the present invention can also be used in prostate cancer cryotherapy. In such cases, a transperineally positioned device having thermal insulation and additional ports for hot water circulation or a device provided with thermal inducible means is utilized, hi the latter case, the device can incorporate a thermal inducible gel or carbon particles that can be heated via a remote radiofrequency source situated in the rectal lumen for example, or by using a magnetic field.

A similar device can be used in thermal ablation treatment of prostate tumors or benign hyperplasia of the prostate. In such cases, intermittent or continuous liquid circulation might be used for cooling the rectal wall and erectile nerves. Additionally, when using a spacer bladder a heat reflective coating on the side facing the prostate might be used to reflect the radiation energy away from the rectum and back towards the prostate.

Exemplary Method for Separator Introduction and Deployment Using TRUS

A method for introducing a controllable dissecting device of the present invention (which may be or include any of the above mentioned designs) and applying thereof for radical prostatectomy and/or for long-term or permanent implantation is described below.

The patient is positioned with the legs in lithotomy position. Guiding system 600 coupled with TRUS probe 617 is used to introduce the device in place. The TRUS probe should be so positioned as to exert minimal pressure on the rectal wall while attaining a chosen or predetermined lateral spreading to the space between the prostate and rectum. In some embodiments, TRUS probe 617 may be angulated for positioning parallel to the lower surface of the prostate as possible. The height and angle of guiding system 600 is adjusted as such that the electronic cursor that is viewed on the captured image from the US monitor is seen to coincide with the inferior margin of the prostate when viewed in longitudinal section. Alternatively, a needle may be guided by the US probe from the perineum without the assistance of the electronic guiding system. A needle introducer having an axial lumen (not shown) is inserted through guiding means 620 until reaching the perineal skin. A sharp needle is then introduced through the introducer lumen and advanced through the perineum. When advanced into tissue the needle path should coincide with the expected path as shown by the electronic cursor. In case of discrepancy, the electronic guiding system may be recalibrated or the difference between the extrapolated real needle path and the electronic path may be taken into account when advancing the needle.

The needle should be advanced at the inferior margin of the prostate until the level of the seminal vesicles. In case that the inferior surface of the prostate is curved, the needle may be advanced initially using the guiding system and then it may be detached from it and may be advanced free hand following the curvature of this margin of the prostate. After advancing the needle to its final position or during its advancement hydro-dissection may be performed to ascertain that the rectal wall is being separated from the lower surface of the prostate. After performing an incision of the perineal skin the dilator is advanced through the guiding system into the perineum and then over the needle until the level of the seminal vesicles.

The entire procedure is optionally performed under continuous monitoring by TRUS. Then the needle may be removed and the folded inflatable device is introduced to the level of the seminal vesicles or the folded inflatable device may be advanced over the needle or over a guide wire to the proper position. The inflatable device is inflated under TRUS monitoring slowly within a few minutes. During this process the width of the rectal all is measured and in case that it reduced to less than 2 to 3 mm the inflation process is stopped and the rectal probe is lowered and or the fluid surrounding the TRUS rectal probe is removed partially, in order to reduce pressure on the rectal wall. After performing these maneuvers the inflation of the balloon is resumed. Such maneuvers may be performed one or more times until full inflation or until the height of the balloon is considered satisfactory by the physician.

In case of permanent implantation the balloon is sealed and the introducer is removed leaving the device in place.

A similar access mode to this space may be used for accessing the peritoneal cavity through the perineum for single port laparoscopy. In this case the needle is advanced through the perineum between the rectum and prostate using the guiding system 600 and TRUS monitoring as mentioned previously. In this case the urinary bladder is drained by a urethral catheter and the needle is advanced through the peritoneum into the peritoneal cavity. In this case, a Veres type needle may be used to safely access the peritoneal cavity. Additionally, an accessory port may be introduced through the anterior abdominal wall; the abdominal cavity may be inflated and the puncturing of the peritoneum and access of the peritoneal cavity by the needle introduced through the perineum may be performed under vision using a miniscope introduced through the anterior abdominal trocar. The dilator and a trocar may be advanced over the needle into peritoneum from the perineum. Alternatively, the tract may be dilated by a dedicated balloon and a trocar may be advanced after that through this tract. Such perineal access and trocar may permit performance of single port laparoscopy in men similar to the surgery performed through the vagina in female patients.

An advantage of such an access is that such perineal incision is much less painful than an abdominal incision, such incision heal very fast and is in a concealed space. These facts are well known by those performing perineal radical prostatectomy which advocate such an approach due to the minimal pain and fast healing of the perineal incision.

In case of temporary placement of a balloon between the prostate and rectum, such as during radical prostatectomy or during a short one session treatment by other modalities as mentioned previously the balloon is left in place for the time of treatment and then removed. The introducer is removed and the inflation tube is left connected to the balloon. The balloon may be deflated until the procedure commence, when the balloon is inflated again through the inflation tube. Such implantation may be performed immediately before the therapeutic procedure.

In case of radical prostatectomy, the needle may be advanced into the bladder after filling the bladder with sterile solution through a urethral catheter. In such case a guide wire may be advanced into the bladder and the device may be advanced over such guide wire up to the level of the seminal vesicles and the guide wire may be removed or it may be left in the tissue to facilitate separation during the operation.

During surgery and after separating the vas deferens and seminal vesicles, the balloon positioned in the proper place is inflated through the inflation tube and the Dennonvilier's fascia covering it is incised over the inflated balloon. Then the vascular supply to the prostate connected to the lateral margins of the prostate is sectioned and closed by clips or diathermia. The inflated balloon facilitates this by separating the prostate from the rectum and tensioning the lateral pedicles of the prostate. Nerve sparing is facilitated by dissecting close to the lateral margins of the prostate while sectioning the lateral pedicles of the prostate. After advancing with this dissection/separation to the level of the urethra and prostate apex, the balloon may be deflated and may be removed. The balloon permits safe and fast separation of the prostate from the rectum, fast sectioning of the lateral pedicles and vascular supply of the prostate and facilitate erectile nerve sparing.

Before removal of the device, the tract of the inflation tube may serve for introducing a grasper a retrieval bag trough the perineum and enlargement of the incision in the perineum may serve for removal of the prostate. After removal of the prostate the perineal incision may be closed and the anastomosis of the bladder neck to the urethra may be performed through the suprapubic incision or using the laparoscopic instruments. Alternatively, the anastomosis may be performed through the perineal incision and then the incision may be closed. Removal of the specimen through a perineal incision may be beneficial since such incision is in a concealed place and is less painful than an abdominal incision. Additionally it may facilitate a fast and more reliable bladder neck to urethra stump anastomosis.

A non-limiting description of a method for tissue dissecting according to an example embodiment of the invention is detailed below.

Figure 10:
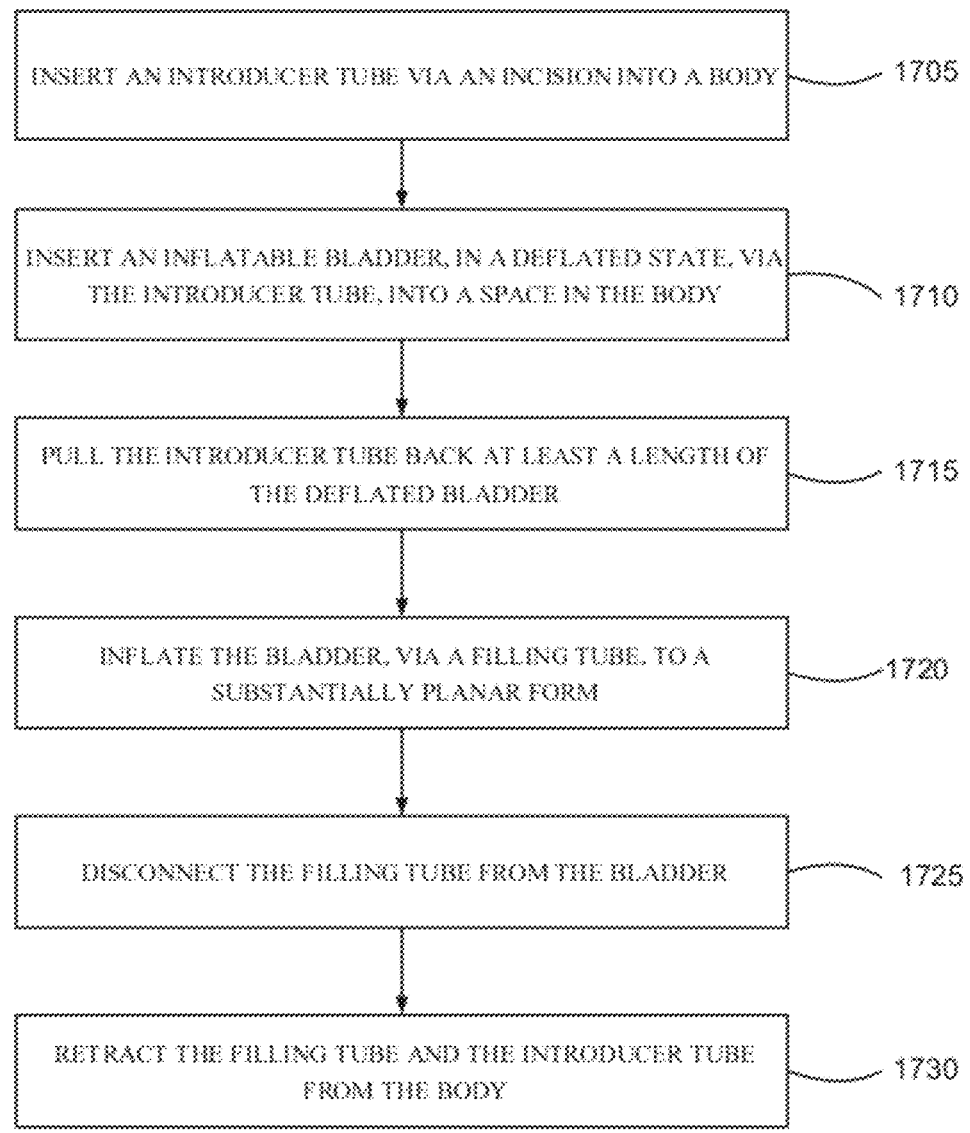
FIG. 10 is a simplified flow chart illustration of a method of tissue dissection according to an example embodiment of the present invention.

Reference is now made to FIG. 10, which is a simplified flow chart illustration of a method of tissue dissection according to an example embodiment of the present invention.

The method includes:
inserting an introducer tube via an incision into a body (1705);
inserting an inflatable bladder, in a deflated state, via the introducer tube, into a space in the body (1710);
pulling the introducer tube back at least a length of the deflated bladder (1715);
inflating the bladder, via a filling tube, to a substantially planar form (1720), thereby dissecting tissue;
disconnecting the filling tube from the bladder (1725);
retracting the filling tube and the introducer tube from the body (1730).

Another example, non-limiting, description of using an exemplary tissue dissecting and/or separating balloon device is detailed below:

Subject Preparation

Prior to implantation, prepare the subject for bowel preparation per local practice (like for colonoscopy) and administer broad spectrum antibiotics. Any anesthesia may be used (local, epidural, general) with or without sedation. With use of anesthesia, other than local, a urethral catheter should be inserted into the bladder at the beginning of the session and left in place until the patient has fully recovered from the anesthesia. A t the end of the procedure (or after recovery from epidural or general anesthesia is used) the catheter should be removed.

The following is described as an example of a free hand approach to the tissue dissection.

Introducer Sheath Insertion

Under TRUS visualization, insert a dedicated needle (through the introducer sheath) connected to a syringe with saline, through the perineal midline, verify that the needle is in the space between the prostate and rectum, and then advance the needle slowly while injecting 5-10 cc of sterile saline for hydrodissection and to delineate the space between the prostate and rectal wall until the needle reaches the prostate base, close to the seminal vesicles.

Perform a 3-5 mm cut around the needle at midline, and under TRUS guidance advance the introducer sheath (that includes an internal dilator) over the needle until it reaches the mark on the needle.

Remove the inner dilator and needle, leaving the introducer sheath in place.

Bladder Insertion

Open the bladder package and extract any air with a syringe.

Introduce the bladder device through the sheath until it reaches the specified mark on the bladder delivery shaft.

While holding the bladder delivery shaft firmly, pull the sheath back to the end of the bladder delivery shaft. At this point the bladder is in situ and exposed, ready for inflation.

Under TRUS guidance, verify the correct location of the bladder. Using the inflation device, inflate the bladder slowly. Continue to monitor location and inflation using TRUS guidance keeping rectal mucosa few mm in width. When optimally inflated by volume, pull back the inflation tube of the bladder shaft to detach the delivery kit from the bladder. This maneuver will seal the bladder.

Perform a rectal examination (DRE) or anuscopy (if deemed necessary) to ascertain rectal mucosa integrity and position of the bladder.

Closing of Incision

Close the incision with a suture if deemed necessary

Immediate Post-Operative Care

Administer analgesics as needed.

Figure 11:
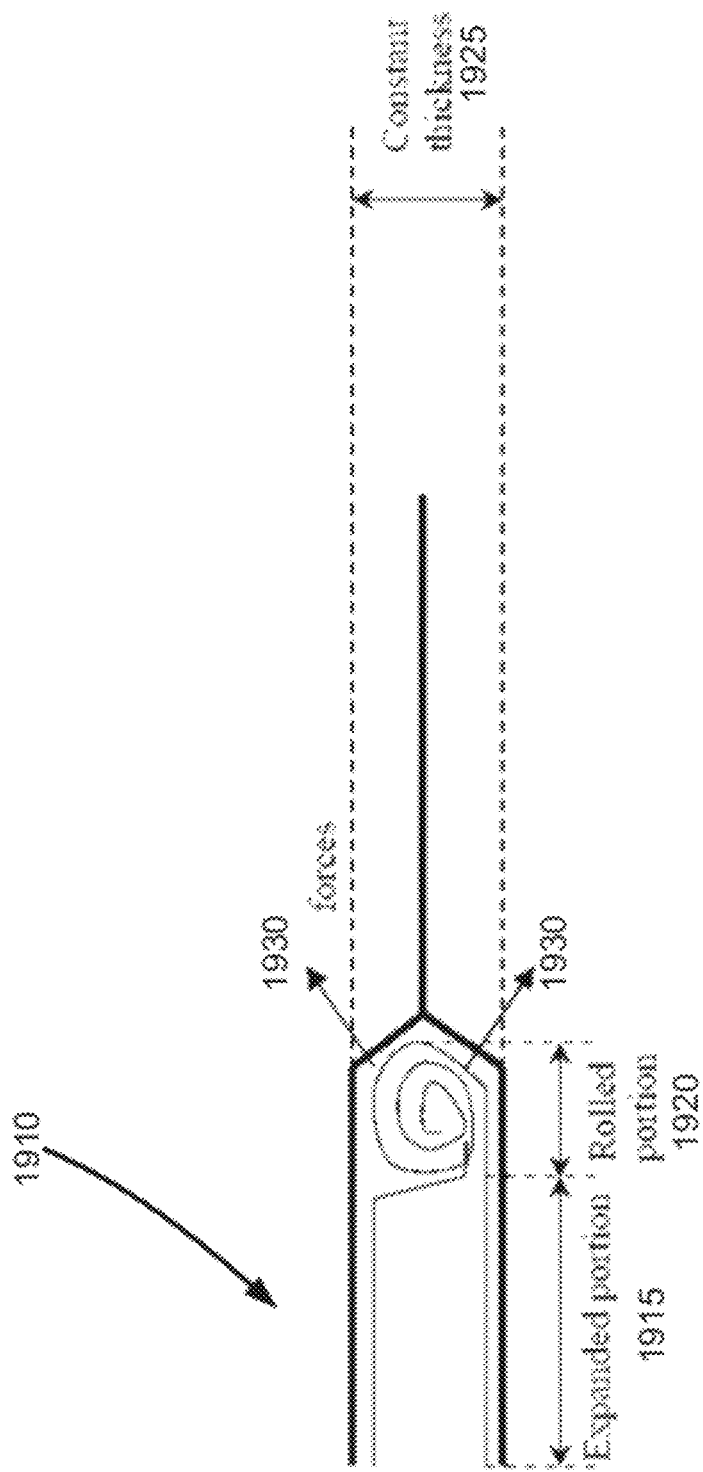
FIG. 11 is a simplified illustration of some forces applied during expansion of an example embodiment of the invention.

Reference is now made to FIG. 11, which is a simplified illustration of some forces applied during expansion of an example embodiment of the invention.

FIG. 11 depicts a portion of an inflatable bladder 1910, similar to the example inflatable bladders such as depicted, for example, in FIGS. 1B, 3A, 3E, 3H-3T. The bladder 1910 is as yet not fully unrolled. A first portion 1915 of the bladder 1910 is already expanded, and a second portion 1920 is still rolled, or unexpanded.

The inflatable bladder 1910 maintains substantially constant thickness 1925.

When the bladder 1910 is additionally inflated, an unrolling, or unfurling, of the second portion 1920 occurs. The unrolling produces forces 1930 acting substantially in direction of the arrows depicting the forces in FIG. 11, causing a dissection, and/or tearing apart of tissue.

As used herein the term "about" refers to ±10%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as "an example" or as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for dissecting tissue of a subject, the method comprising: providing a tissue dissecting device comprising: an inflatable bladder comprising a port disposed at a proximal end of the inflatable bladder and a ring disposed on the bladder at a distal end thereof; an introducer tube comprising an inflation lumen, detachably connected or connectable to said inflatable bladder such that said inflation lumen is in direct communication with said port, and configured for guiding said inflatable bladder in a deflated state to an anatomic target location in the subject's body and inflating said inflatable bladder via said port; and an elongated strip having first and second ends; the method further comprising: (a) inserting said inflatable bladder, in said deflated state, readily connected to said introducer tube, in between tissues in said anatomic target location in the subject's body; (b) at a time when the elongated strip is releasably connected at its first end to the ring and is connected at its second end to the introducer tube, inflating said inflatable bladder to a substantially planar form thereby dissecting in between said tissues wherein during said inflation a presence of the elongated strip restricts the inflatable bladder in lateral displacement and (c) detaching said introducer tube from said inflatable bladder; and (d) withdrawing said introducer tube and said elongated strip from the subject's body, thereby leaving said inflatable bladder in said anatomic target location.

2. The method according to claim 1, wherein said inflation is performed by injecting liquid into said inflatable bladder.

3. The method according to claim 1, further comprising creating an opening in-between tissue layers.

4. The method according to claim 1, further comprising creating a hydrodissected tissue space between a prostate and a rectal wall.

5. The method according to claim 1, wherein said detaching comprises sealing said inflatable bladder.

6. The method according to claim 1 in which dissecting in between said tissues comprises dissecting connecting tissue between organs.

7. The method according to claim 1 in which the deflated state comprises a rolled-up bladder.

8. The method according to claim 1 in which said inflatable bladder is configured to unroll when inflated, thereby to dissect the tissue by elongation of the compact state of the bladder.

9. The method according to claim 1 in which a thickness of said inflatable bladder is substantially constant throughout the inflating.

10. The method according to claim 1 wherein:

i. the substantially planar form of the inflatable bladder defines two opposing faces, and the inflatable bladder includes at least one through-hole traversing a thickness of the bladder to connect the two opposing faces to each other; and ii. a presence of the at least one through-hole limits a maximum thickness of said inflatable bladder.

* * * * *